(12) United States Patent
Tanimoto et al.

(10) Patent No.: US 11,101,427 B2
(45) Date of Patent: Aug. 24, 2021

(54) PIEZOELECTRIC SUBSTRATE, SENSOR, ACTUATOR, BIOLOGICAL INFORMATION ACQUISITION DEVICE, AND PIEZOELECTRIC FIBER STRUCTURE

(71) Applicant: Mitsui Chemicals, Inc., Tokyo (JP)

(72) Inventors: Kazuhiro Tanimoto, Nagoya (JP); Mitsunobu Yoshida, Nagoya (JP); Katsuki Onishi, Nagoya (JP)

(73) Assignee: MITSUI CHEMICALS, INC., Tokyo (JP)

(*) Notice: Subject to any disclaimer, the term of this patent is extended or adjusted under 35 U.S.C. 154(b) by 182 days.

(21) Appl. No.: 16/348,590

(22) PCT Filed: Nov. 17, 2017

(86) PCT No.: PCT/JP2017/041488
§ 371 (c)(1),
(2) Date: May 9, 2019

(87) PCT Pub. No.: WO2018/092886
PCT Pub. Date: May 24, 2018

(65) Prior Publication Data
US 2020/0058844 A1 Feb. 20, 2020

(30) Foreign Application Priority Data
Nov. 18, 2016 (JP) ............... JP2016-225366

(51) Int. Cl.
*H01L 41/193* (2006.01)
*G01L 1/16* (2006.01)
(Continued)

(52) U.S. Cl.
CPC .............. *H01L 41/193* (2013.01); *G01L 1/16* (2013.01); *H01L 41/09* (2013.01); *H01L 41/1132* (2013.01); *H01L 41/45* (2013.01)

(58) Field of Classification Search
CPC ... H01L 41/193; H01L 41/09; H01L 41/1132; G01L 1/16
See application file for complete search history.

(56) References Cited

U.S. PATENT DOCUMENTS

| | | |
|---|---|---|
| 2012/0025674 A1 | 2/2012 | Yoshida et al. |
| 2012/0132846 A1 | 5/2012 | Yoshida et al. |
| | (Continued) | |

FOREIGN PATENT DOCUMENTS

| | | |
|---|---|---|
| EP | 3 376 549 A1 | 9/2018 |
| EP | 3 471 159 A1 | 4/2019 |
| | (Continued) | |

OTHER PUBLICATIONS

International Search Report (PCT/ISA/210) and Written Opinion (PCT/ISA/237) dated Feb. 13, 2018, by the Japanese Patent Office as the International Searching Authority for International Application No. PCT/JP2017/041488.
(Continued)

*Primary Examiner* — J. San Martin
(74) *Attorney, Agent, or Firm* — Buchanan, Ingersoll & Rooney PC

(57) ABSTRACT

Provided is a piezoelectric substrate, containing an elongate piezoelectric body that is helically wound, in which the piezoelectric body includes an optically active polypeptide, a length direction of the piezoelectric body and a main orientation direction of the optically active polypeptide included in the piezoelectric body are substantially parallel to each other, and the piezoelectric body has a degree of orientation F of from 0.50 to less than 1.00, as determined from X-ray diffraction measurement by the following Formula (a):

$$\text{Degree of orientation } F=(180°-\alpha)/180° \quad (a)$$

(Continued)

in Formula (a), α represents a half width (°) of a peak derived from orientation.

19 Claims, 6 Drawing Sheets

(51) Int. Cl.
  *H01L 41/09* (2006.01)
  *H01L 41/113* (2006.01)
  *H01L 41/45* (2013.01)

(56) References Cited

U.S. PATENT DOCUMENTS

| | | | |
|---|---|---|---|
| 2015/0141618 A1 | 5/2015 | Ishikawa et al. | |
| 2015/0202351 A1* | 7/2015 | Kaplan | A61L 31/10 607/116 |
| 2017/0331027 A1* | 11/2017 | Kim | H01L 41/193 |
| 2018/0108826 A1* | 4/2018 | Tajitsu | D03D 1/0088 |
| 2018/0358541 A1* | 12/2018 | Tajitsu | H01L 41/082 |
| 2019/0003905 A1* | 1/2019 | Yoshida | H01L 41/082 |
| 2019/0214542 A1* | 7/2019 | Yoshida | G01L 1/16 |
| 2019/0267538 A1* | 8/2019 | Yoshida | H01L 41/333 |
| 2019/0273199 A1* | 9/2019 | Tajitsu | D04B 21/20 |
| 2019/0281820 A1* | 9/2019 | Usui | A01N 37/02 |
| 2020/0020846 A1* | 1/2020 | Tanimoto | H01L 41/193 |
| 2020/0362484 A1* | 11/2020 | Kanematsu | H01L 41/113 |

FOREIGN PATENT DOCUMENTS

| | | |
|---|---|---|
| JP | H10132669 A | 5/1998 |
| JP | 4934235 B2 | 5/2012 |
| JP | 2014029054 A | 2/2014 |
| JP | 2014227410 A | 12/2014 |
| WO | 2010104196 A1 | 9/2010 |
| WO | 2012/047682 A2 | 4/2012 |
| WO | 2014058077 A1 | 4/2014 |
| WO | 2016027613 A1 | 2/2016 |
| WO | 2016175321 A1 | 11/2016 |
| WO | 2017/213108 A1 | 12/2017 |

OTHER PUBLICATIONS

Farrar et al., "Permanent Polarity and Piezoelectricity of Electrospun α-Helical Poly(α-Amino Acid) Fibers", Advanced Materials, (Jul. 28, 2011), vol. 23, No. 34, pp. 3954-3958, XP055006196.

The Extended European Search Report dated May 25, 2020, by the European Patent Office in corresponding European Patent Application No. 17872372.2. (8 pages).

Notice of Reasons for Rejection dated Apr. 21, 2020, by the Japanese Patent Office in corresponding Japanese Patent Application No. 2018-551710 and an English translation of the Notice. (11 pages).

* cited by examiner

PIEZOELECTRIC SUBSTRATE, SENSOR, ACTUATOR, BIOLOGICAL INFORMATION ACQUISITION DEVICE, AND PIEZOELECTRIC FIBER STRUCTURE

TECHNICAL FIELD

The present disclosure relates to a piezoelectric substrate, a sensor, an actuator, a biological information acquisition device, and a piezoelectric fiber structure.

BACKGROUND ART

In recent years, it has been examined to apply a helical chiral polymer-containing piezoelectric body to piezoelectric devices such as sensors and actuators. In such piezoelectric devices, film-form piezoelectric bodies are used.

As for the helical chiral polymer in the piezoelectric body, the use of an optically active polymer, such as a synthetic polypeptide (e.g., poly(γ-benzyl glutarate) or poly(γ-methyl glutarate)) or a polylactic acid polymer, has been drawing attention. Particularly, it is known that polylactic acid polymers are allowed to express piezoelectricity only by a mechanical stretching operation. It is also known that piezoelectric bodies containing a polylactic acid polymer do not require a poling treatment and that their piezoelectricity are not deteriorated over several years.

For example, as polylactic acid polymer-containing piezoelectric bodies, those having a large piezoelectric constant ($d_{14}$) and excellent transparency have been reported (see, for example. Japanese Patent No. 4934235 and WO 2010/104196).

In addition, recently, attempts have been made to utilize a conductor by coating it with a piezoelectric material.

For example, piezo cables constituted by a central conductor, a piezoelectric material layer, an outer conductor, and an outer cover that are sequentially and coaxially arranged from the center to the outer side are known (see, for example. Japanese Patent Application Laid-Open (JP-A) No. H10-132669).

Further, piezoelectric units in which conductive fibers are coated with a fiber composed of a piezoelectric polymer containing polyvinylidene fluoride or polylactic acid are known (see, for example, WO 2014/058077).

Meanwhile, natural polymers, such as cellulose, amylose and natural polypeptides (proteins) are known to have optical activities and exhibit piezoelectricity due to the occurrence of orientation in the process of being produced in the natural world (see, for example, J. Phys. Soc. Jpn. 10 (1955) 149, Polym. Phys. 18 (1980) 1609, and J. Phys. Soc. Jpn. 12 (1957) 1158).

SUMMARY OF INVENTION

Technical Problem

Incidentally, when a film-form piezoelectric body (e.g., any of the piezoelectric bodies described in Examples of Japanese Patent No. 4934235 and WO 2010/104196) is used in a largely irregular place or a place with a large amount of deformation (e.g., when such a piezoelectric body is used as a part or the entirety of a wearable product), damages such as breakage and wrinkling occur in the piezoelectric body due to deformation, and this may consequently reduce the piezoelectric sensitivity (e.g., the sensor sensitivity when the piezoelectric body is used as a sensor, or the dynamic sensitivity when the piezoelectric body is used as an actuator: the same applies below).

In addition, JP-A No. H10-132669 discloses a piezo cable constituted by, as described above, a central conductor, a piezoelectric material layer, an outer conductor, and an outer cover that are sequentially and coaxially arranged from the center to the outer side, and describes polyvinylidene fluoride (PVDF) as a piezoelectric material. However, PVDF shows fluctuations in piezoelectric constant over time, and the piezoelectric constant may be reduced with time. Further, since PVDF is a ferroelectric substance and thus pyroelectric, its piezoelectric signal output may fluctuate due to a change in ambient temperature. Therefore, the piezo cable disclosed in JP-A No. H10-132669 may be insufficient in terms of the stability in piezoelectric sensitivity (stability against time or temperature change), namely the durability.

Moreover, in WO 2014/058077, only polyvinylidene fluoride and polylactic acid are exemplified as piezoelectric polymers used in fibers composed of a piezoelectric polymer, and it is described that polylactic acid is preferred.

However, since polylactic acid is a biodegradable resin and is hydrolyzed in a high-temperature and high-humidity environment, utilization thereof may be difficult especially in those fields where high durability is required (e.g., the field of in-vehicle applications).

One embodiment of the present invention has been made in view of the above-described circumstances.

That is, an object of one embodiment of the invention is to provide: a piezoelectric substrate having excellent durability; and a sensor, an actuator, a biological information acquisition device and a piezoelectric fiber structure, which include the piezoelectric substrate.

Solution to Problem

Specific means for achieving the above-described object include the following modes.

<1> A piezoelectric substrate including an elongate piezoelectric body that is helically wound, wherein the piezoelectric body includes an optically active polypeptide, a length direction of the piezoelectric body and a main orientation direction of the optically active polypeptide included in the piezoelectric body are substantially parallel to each other, and the piezoelectric body has a degree of orientation F of from 0.50 to less than 1.00, as determined from X-ray diffraction measurement by the following Formula (a):

$$\text{Degree of orientation } F = (180° - \alpha)/180° \tag{a}$$

wherein, in Formula (a), a represents a half width (°) of a peak derived from orientation.

<2> The piezoelectric substrate according to <1>, wherein the elongate piezoelectric body is helically wound in a single direction.

<3> The piezoelectric substrate according to <1> or <2>, further including an elongate core material, wherein the elongate piezoelectric body is helically wound around the elongate core material.

<4> The piezoelectric substrate according to <3>, wherein the elongate core material is a conductor.

<5> The piezoelectric substrate according to <3> or <4>, including an outer conductor on an outer peripheral side of the elongate piezoelectric body, wherein the elongate core material and the outer conductor are electrically insulated from each other.

<6> The piezoelectric substrate according to <1> or <2>, including no core material.

<7> The piezoelectric substrate according to any one of <1> to <6>, wherein the optically active polypeptide has a β sheet structure.

<8> The piezoelectric substrate according to any one of <1> to <7>, wherein the elongate piezoelectric body includes a fiber that is composed of the optically active polypeptide.

<9> The piezoelectric substrate according to any one of <1> to <8>, wherein the optically active polypeptide includes at least one of fibroin or a spider silk protein.

<10> The piezoelectric substrate according to any one of <1> to <9>, wherein the fiber that is composed of the optically active polypeptide includes at least one of a silk or a spider silk.

<11> The piezoelectric substrate according to <10>, wherein the silk is a refined silk.

<12> The piezoelectric substrate according to any one of <1> to <11>, wherein the elongate piezoelectric body is composed of a fiber that is composed of the optically active polypeptide, and the fiber is a yarn having a number of twists of 500 T/m or less.

<13> The piezoelectric substrate according to any one of <1> to <12>, wherein the elongate piezoelectric body is wound at a helix angle of from 20° to 70°.

<14> The piezoelectric substrate according to any one of <1> to <13>, including an insulator on the outermost periphery.

<15> A sensor including the piezoelectric substrate according to any one of <1> to <14>.

<16> An actuator including the piezoelectric substrate according to any one of <1> to <14>.

<17> A biological information acquisition device including the piezoelectric substrate according to any one of <1> to <14>.

<18> A piezoelectric fiber structure including:
a first piezoelectric substrate, which is the piezoelectric substrate according to any one of <1> to <14>; and
a second piezoelectric substrate, which is the piezoelectric substrate according to any one of <1> to <14>, in which an optically active polypeptide included in a piezoelectric body has the same chirality as an optically active polypeptide included in a piezoelectric body of the first piezoelectric substrate, and a winding direction of the piezoelectric body is opposite to that of the piezoelectric body of the first piezoelectric substrate.

<19> A piezoelectric fiber structure including:
a first piezoelectric substrate, which is the piezoelectric substrate according to any one of <1> to <14>; and
a second piezoelectric substrate, which is the piezoelectric substrate according to any one of <1> to <14>, in which an optically active polypeptide included in a piezoelectric body has a chirality that is different from that of an optically active polypeptide included in a piezoelectric body of the first piezoelectric substrate, and a winding direction of the piezoelectric body is the same as that of the piezoelectric body of the first piezoelectric substrate.

Advantageous Effects of Invention

According to one embodiment of the invention, a piezoelectric substrate having excellent durability, as well as a sensor, an actuator and a biological information acquisition device, which include the piezoelectric substrate, are provided.

In addition, according to another embodiment of the invention, a piezoelectric fiber structure that includes the piezoelectric substrate and thereby exhibits excellent antibacterial performance, and a production method of the same, as well as a piezoelectric woven fabric and a piezoelectric knitted fabric, which include the piezoelectric fiber structure, can be provided.

DETAILED DESCRIPTION OF THE INVENTION

Mode for Carrying Out the Invention

Figure 1A:
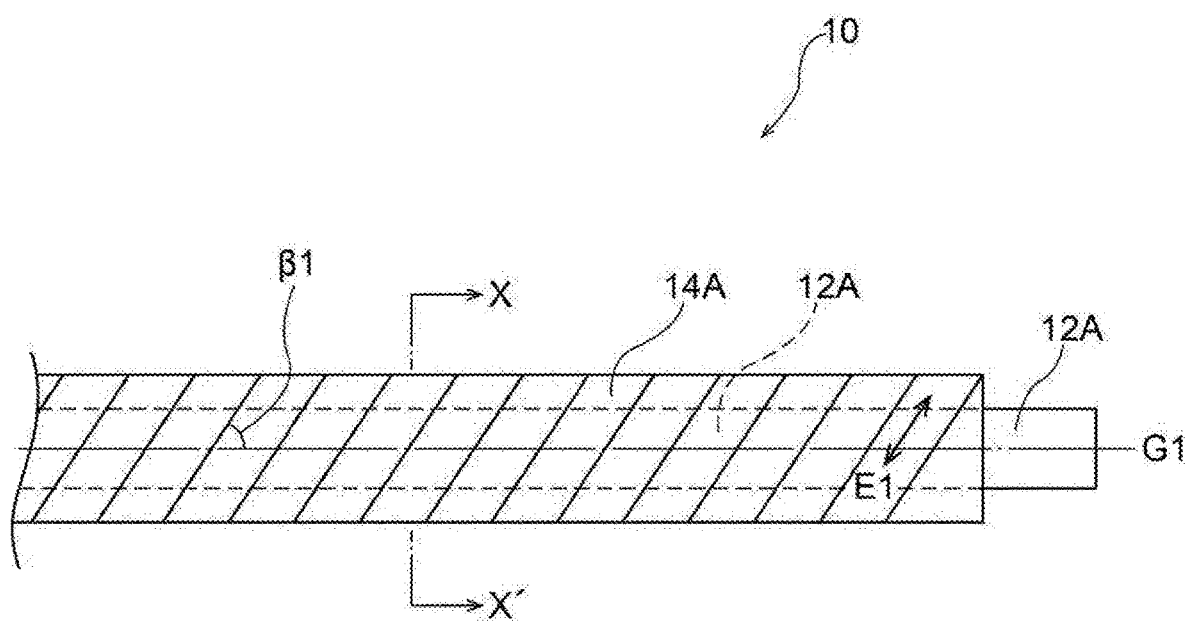
FIG. 1A is a side view schematically illustrating a piezoelectric substrate according to a specific example of a first mode.

In the present specification, those numerical ranges that are stated with "to" each denote a range that includes the numerical values stated before and after "to" as the lower and upper limit values, respectively.

[Piezoelectric Substrate]

A piezoelectric substrate according to one embodiment includes an elongate piezoelectric body that is helically wound. The piezoelectric body includes an optically active polypeptide, a length direction of the piezoelectric body and a main orientation direction of the optically active polypeptide included in the piezoelectric body are substantially parallel to each other, and the piezoelectric body has a degree of orientation F of from 0.50 to less than 1.00, as determined from X-ray diffraction measurement by the following Formula (a):

$$\text{Degree of orientation } F=(180°-\alpha)/180° \quad (a)$$

wherein, in Formula (a), α represents a half width (°) of a peak derived from orientation.

The piezoelectric substrate according to one embodiment expresses piezoelectricity (e.g., piezoelectric sensitivity) because:

the elongate piezoelectric body is helically wound:

the elongate piezoelectric body includes an optically active polypeptide;

the length direction of the elongate piezoelectric body and the main orientation direction of the optically active polypeptide included in the elongate piezoelectric body are substantially parallel to each other; and the degree of orientation F is in a range of from 0.5 to less than 1.0.

Further, the piezoelectric substrate according to one embodiment includes an optically active polypeptide having excellent hydrolysis resistance in a high-temperature and high-humidity environment and, therefore, exhibits excellent durability (particularly in a high-temperature and high-humidity environment) as compared to, for example, a piezoelectric substrate containing a polylactic acid.

In the present specification, the term "excellent durability" means that a reduction in the piezoelectric sensitivity is suppressed (particularly in a high-temperature and high-humidity environment).

<Piezoelectric Body>

The piezoelectric substrate includes an elongate piezoelectric body.

The degree of orientation F of the elongate piezoelectric body is in a range of from 0.50 to less than 1.00.

The degree of orientation F of the piezoelectric body is a value determined from X-ray diffraction measurement by the following Formula (a) and means a C-axis orientation degree.

$$\text{Degree of orientation } F=(180°-\alpha)/180° \quad (a)$$

wherein, in Formula (a), a represents a half width (°) of a peak derived from orientation.

The degree of orientation F is an index that indicates the degree of orientation of the optically active polypeptide included in the piezoelectric body.

In the piezoelectric substrate, the feature that the degree of orientation F of the elongate piezoelectric body is 0.50 or more contributes to the expression of the piezoelectricity.

The feature that the degree of orientation F of the elongate piezoelectric body is less than 1.00 contributes to the productivity of the piezoelectric body.

The degree of orientation F of the elongate piezoelectric body is preferably from 0.50 to 0.99, more preferably from 0.70 to 0.98, particularly preferably from 0.80 to 0.97.

In the piezoelectric substrate, the feature that the length direction of the piezoelectric body and the main orientation direction of the optically active polypeptide included in the piezoelectric body are substantially parallel to each other also contributes to the expression of the piezoelectricity.

The feature that the length direction of the piezoelectric body and the main orientation direction of the optically active polypeptide included in the piezoelectric body are substantially parallel to each other is also advantageous in that it allows the piezoelectric body to have excellent tensile strength in its length direction. Therefore, the piezoelectric body is unlikely to be broken when helically wound.

The term "substantially parallel" used herein means that, when an angle formed by two lines is indicated in a range of from 0° to 90°, the angle formed by the two lines is from 0° to smaller than 30° (preferably from 0° to 22.5°, more preferably from 0° to 10°, still more preferably from 0° to 5°, particularly preferably from 0° to 3°).

For example, when the piezoelectric body is a silk or a spider silk, the length direction of the piezoelectric body (the silk or the spider silk) and the main orientation direction of the optically active polypeptide (e.g., fibroin or a spider silk protein) included in the piezoelectric body are substantially parallel to each other in the generation process of the silk or the spider silk.

Whether or not the length direction of the piezoelectric body and the main orientation direction of the optically active polypeptide included in the piezoelectric body are substantially parallel to each other can be confirmed by comparing the sample placement direction and the azimuthal angle of a crystal peak in X-ray diffraction measurement.

In the piezoelectric substrate, the feature that the piezoelectric body includes an optically active polypeptide also contributes to the expression of the piezoelectricity.

In addition, as described above, the optically active polypeptide has excellent hydrolysis resistance; therefore, the piezoelectric body containing such an optically active polypeptide leads to superior durability of the piezoelectric body and the piezoelectric substrate as compared to a piezoelectric body containing a polylactic acid as a main component.

Moreover, as described above, the optically active polypeptide is not pyroelectric; therefore, the piezoelectric body containing such an optically active polypeptide also leads to superior durability of the piezoelectric body and the piezoelectric substrate as compared to a piezoelectric body containing a PVDF as a main component.

The term "optically active polypeptide" used herein means a polypeptide having an optical activity (i.e., a polypeptide which has asymmetric carbon atoms and is biased in terms of the amounts of optical isomers).

The optically active polypeptide preferably has a β sheet structure from the standpoints of piezoelectricity and strength.

Examples of the optically active polypeptide include animal proteins having an optical activity (e.g., fibroin, sericin, collagen, keratin, elastin, and spider silk proteins).

It is preferred that the optically active polypeptide includes at least one of fibroin or a spider silk protein, and it is particularly preferred that the optically active polypeptide is composed of at least one of fibroin or a spider silk protein.

The spider silk protein is not particularly restricted as long as it is a natural spider silk protein, or a protein derived from or analogous to (hereinafter, simply referred to as "derived from") a natural spider silk protein.

It is noted here that the "protein derived from a natural spider silk protein" is a protein having an amino acid sequence that is the same as or analogous to the amino acid repetitive sequence of the natural spider silk protein.

Examples of the "protein derived from a natural spider silk protein" include recombinant spider silk proteins, variants of natural spider silk proteins, analogs of natural spider silk proteins, and derivatives of natural spider silk proteins.

In terms of excellent tenacity, the spider silk protein is preferably a major dragline silk protein produced in major ampullate glands of a spider or a spider silk protein derived from a major dragline silk protein.

Examples of the major dragline silk proteins include major ampullate spidroin MaSp1 and MaSp2 derived from golden silk spider (*Nephila clavipes*), and ADF3 and ADF4 derived from European garden spider (*Araneus diadematus*).

The spider silk protein may also be a minor dragline silk protein produced in minor ampullate glands of a spider, or a spider silk protein derived from a minor dragline silk protein.

Examples of the minor dragline silk proteins include minor ampullate spidroin MiSp1 and MiSp2 derived from golden silk spider (*Nephila clavipes*).

Other than the above, the spider silk protein may also be a flagelliform silk protein produced in flagelliform glands of a spider, or a spider silk protein derived therefrom.

Examples of the flagelliform silk proteins include flagelliform silk proteins derived from golden silk spider (*Nephila clavipes*).

Examples of the above-described spider silk protein derived from a major dragline silk protein include recombinant spider silk proteins containing an amino acid sequence unit represented by the following Formula (1).

The recombinant spider silk proteins may contain two or more (preferably four or more, more preferably six or more) units of an amino acid sequence represented by the following Formula (1).

When the recombinant spider silk proteins contain two or more units of an amino acid sequence represented by the following Formula (1), the two or more units of an amino acid sequence may be the same or may be different from each other.

$$REP1-REP2 \qquad (1)$$

In the Formula (1), the REP1 is a polyalanine region that is mainly constituted by alanine and represented by (X1)p; and REP2 is an amino acid sequence composed of from 10 to 200 amino acid residues.

In Formula (1), REP1 is a polyalanine region that is mainly constituted by alanine and represented by (X1)p. REP1 is preferably a polyalanine.

In (X1)p, p is not particularly restricted; however, p represents preferably an integer of 2 to 20, more preferably an integer of 4 to 12.

In (X1)p, X1 represents alanine (Ala), serine (Ser), or glycine (Gly).

In the polyalanine region represented by (X1)p, the total number of alanine residues is preferably 80% or more (more preferably 85% or more), with respect to the total number of amino acid residues in the polyalanine region.

In REP1 of Formula (1), the number of alanine residues arranged in succession is preferably 2 or more, more preferably 3 or more, further preferably 4 or more, and particularly preferably 5 or more.

Further, in REP1 of Formula (1), the number of alanine residues arranged in succession is preferably 20 or less, more preferably 16 or less, still more preferably 12 or less, particularly preferably 10 or less.

In Formula (1), REP2 is an amino acid sequence composed of from 10 to 200 amino acid residues. The total number of residues of glycine, serine, glutamine, proline and alanine that are contained in the amino acid sequence is preferably 40% or more, more preferably 50% or more, particularly preferably 60% or more, with respect to the total number of amino acid residues contained therein.

Examples of the above-described spider silk protein derived from a minor dragline silk protein include recombinant spider silk proteins containing an amino acid sequence represented by the following Formula (2).

$$REP3-REP4-REP5 \qquad (2)$$

In Formula (2), REP3 is an amino acid sequence represented by (Gly-Gly-Z)m, REP4 is an amino acid sequence represented by (Gly-Ala)l, and REP5 is an amino acid sequence represented by (Ala)r; Z in REP3 means any one of amino acids; m in REP3 is from 1 to 4; l in REP4 is from 0 to 4; and r in REP5 is from 1 to 6.

In REP3, Z means any one of amino acids and is particularly preferably an amino acid selected from the group consisting of Ala, Tyr and Gin.

The above-described recombinant spider silk proteins (e.g., the recombinant spider silk proteins containing a unit of the amino acid sequence represented by Formula (1), and the recombinant spider silk proteins containing the amino acid sequence represented by Formula (2)) can be produced using a host that has been transformed with an expression vector containing a gene encoding a natural spider silk protein to be recombined.

The elongate piezoelectric body preferably includes a fiber composed of an optically active polypeptide from the standpoint of piezoelectricity.

Examples of the fiber composed of an optically active polypeptide include fibers composed of animal proteins having an optical activity (e.g., silk, wool, mohair, cashmere, camel, llama, alpaca, vicuna, angora, and spider silks).

From the standpoint of piezoelectricity it is preferred that the fiber composed of an optically active polypeptide includes at least one of a silk or a spider silk, and it is particularly preferred that the fiber composed of an optically active polypeptide is composed of at least one of a silk or a spider silk.

Examples of the silk include raw silks, refined silks, reformed silks, and fluorescent silks.

The silk is preferably a raw silk or a refined silk, particularly preferably a refined silk.

The term "refined silk" used herein means a silk obtained by removing sericin from a raw silk having a double structure of sericin and fibroin, and the term "refine" used herein means an operation of removing sericin from a raw silk. The color of a raw silk is non-glossy white; however, removal of sericin from the raw silk (i.e., by refining) causes the color to change from non-glossy white to glossy silver-white. In addition, a soft texture is increased by the refining.

From the standpoint of piezoelectricity, the elongate piezoelectric body preferably includes a long fiber composed of an optically active polypeptide. This is believed to be because such a long fiber, as compared to a short fiber, allows a stress applied to the piezoelectric substrate to be more easily transmitted to the piezoelectric body.

The term "long fiber" used herein means a fiber having such a length that can be continuously wound from one end to the other end of the piezoelectric substrate along the longitudinal direction.

The above-mentioned silk, wool, mohair, cashmere, camel, llama, alpaca, vicuna, angora, and spider silks all correspond to long fibers.

Among long fibers, a silk and a spider silk are preferred from the standpoint of piezoelectricity.

When the elongate piezoelectric body includes any of the above-described fibers, the elongate piezoelectric body preferably includes at least one yarn composed of at least one fiber described above.

Examples of a mode in which the elongate piezoelectric body includes any of the above-described fibers include one in which the elongate piezoelectric body is composed of a single fiber described above, and a mode in which the elongate piezoelectric body is composed of an assembly of plural fibers described above.

The yarn may be a twisted yarn or a non-twisted yarn; however, from the standpoint of piezoelectricity, the yarn is preferably a yarn having a number of twists of 500 T/m or less (i.e., a twisted yarn having a number of twists of 500 T/m or less, or a non-twisted yarn (number of twists=0 T/m)).

Examples of the non-twisted yarn include a single raw yarn, and an assembly of plural raw yarns.

The thickness of the elongate piezoelectric body (when the elongate piezoelectric body is an assembly of plural yarns, the thickness of the whole assembly) is not particularly restricted; however, it is preferably from 0.0001 to 2 mm, more preferably from 0.001 to 1 mm, particularly preferably from 0.005 to 0.8 mm.

When the elongate piezoelectric body is a single raw yarn or an assembly of plural raw yarns, the fineness of each raw yarn is preferably from 0.01 to 10,000 denier, more preferably from 0.1 to 1,000 denier, particularly preferably from 1 to 100 denier.

In the piezoelectric substrate, the elongate piezoelectric body is wound helically.

In the piezoelectric substrate, a charge is generated when a shear stress is applied to the helically-wound elongate piezoelectric body. As a result, piezoelectricity is expressed.

A shear stress can be applied to the piezoelectric body by, for example, pulling the entirety of the helically-wound elongate piezoelectric body in the direction of the helical axis, twisting a part of the helically-wound elongate piezoelectric body (i.e., twisting a part of the piezoelectric body around the helical axis), or bending a part or the entirety of the helically-wound elongate piezoelectric body.

The piezoelectric substrate may or may not include a core material.

The first mode of the piezoelectric substrate is a mode in which the piezoelectric substrate further includes an elongate core material, and the elongate piezoelectric body is helically wound around the elongate core material.

The second mode of the piezoelectric substrate is a mode in which the piezoelectric substrate does not include a core material, and the elongate piezoelectric body is helically wound around an imaginary helical axis (i.e., an imaginary central axis of a helical structure).

Preferred modes of each of the first and the second modes will be described in the section of "Core Material and Outer Conductor" below.

The elongate piezoelectric body is preferably wound at a helix angle of from 20° to 70°.

The term "helix angle" used herein means an angle formed by the helical axis direction (when the elongate piezoelectric body includes a core material, the length direction of the core material) and the length direction of the piezoelectric body that is wound (see a helix angle β1 in FIG. 1A).

The helix angle is preferably from 25° to 65°, more preferably from 30° to 60°, particularly preferably from 35° to 55°.

It is preferred that the elongate piezoelectric body is helically wound in a single direction.

The phrase "helically wound in a single direction" used herein means that:

when viewed from one end of the piezoelectric substrate, the piezoelectric body is helically wound in a left-handed (i.e., counterclockwise) manner from the front side toward the back side; or when viewed from one end of the piezoelectric substrate, the piezoelectric body is helically wound in a right-handed (i.e., clockwise) manner from the front side toward the back side.

In cases where the elongate piezoelectric body is helically wound in a single direction, a phenomenon that the polarities of generated charges are cancelled with each other (i.e., a phenomenon that the piezoelectricity is deteriorated) is suppressed. Therefore, the piezoelectricity of the piezoelectric substrate is further improved.

The mode in which the piezoelectric substrate includes the elongate piezoelectric body that is helically wound in a single direction encompasses not only a mode in which the piezoelectric substrate includes only a single layer of the piezoelectric body, but also a mode in which the piezoelectric body is disposed in plural layers.

Examples of the mode in which the piezoelectric body is disposed in plural layers include a mode in which the piezoelectric body of a first layer is helically wound in a single direction and the piezoelectric body of a second layer is further helically wound thereon in the same single direction.

Examples of modes of the piezoelectric substrate also include a mode in which the piezoelectric substrate includes, as elongated piezoelectric bodies: a first piezoelectric body that is helically wound in a single direction; and a second piezoelectric body that is helically wound in a direction different from the single direction, and the chirality of the optically active polypeptide included in the first piezoelectric substrate and that of the optically active polypeptide included in the second piezoelectric body are different from each other.

Examples of modes of the piezoelectric substrate further include a mode in which the piezoelectric substrate includes: a first elongate body that is an elongate piezoelectric body helically wound in a single direction; and a second elongate body that is an elongate piezoelectric body or a fiber other than a piezoelectric body, which is helically wound in a direction different from the single direction.

The first elongate body and the second elongate body may form a braided structure in which they alternately intersect with each other.

When the second elongate body is a piezoelectric body, the chirality of the optically active polypeptide included in the first elongate body and that of the optically active polypeptide included in the second elongate body may be the same or different from each other.

The piezoelectric body may also include a component other than the optically active polypeptide as required.

For example, when the piezoelectric body is an assembly of plural raw yarns, the piezoelectric body may include an adhesive for immobilization of the assembly of plural raw yarns. A preferred mode of the adhesive will be described below.

<Core Material and Outer Conductor>

(Piezoelectric Substrate of First Mode)

The piezoelectric substrate of the first mode includes an elongate core material.

In the piezoelectric substrate of the first mode, the elongate piezoelectric body is helically wound around the elongate core material.

The core material may be a conductor or a non-conductor.

The core material may be a non-conductor.

A mode in which the piezoelectric substrate includes a core material that is a non-conductor is advantageous in terms of resistance to repeated deformation (i.e., avoidance of fatigue fracture of a metal wire) as compared to a mode in which the piezoelectric substrate includes a core material that is a metal wire.

The core material that is a non-conductor is not particularly restricted as long as it is a non-electroconductive core material, and examples thereof include polymer resins, such as polyamide resins (e.g., nylon resins and aramid resins), polyester resins, acrylic resins, polyethylene resins, polypropylene resins, polyvinyl chloride resins, polysulfone resins, polyether resins, and polyurethane resins; cellulose-based resins; and inorganic materials, such as glass, silica gel, and ceramics. These materials may be used singly, or in combination of two or more kinds thereof.

The core material that is a non-conductor is preferably a fiber-form core material composed of a single or plural bundles.

Examples of the fiber-form core material include yarns (monofilament yarns and multifilament yarns).

The core material may be a conductor as well.

A mode in which the piezoelectric substrate includes a core material that is a conductor has an advantage in that an electrical signal (a voltage signal or a charge signal) can be easily extracted from the piezoelectric body through the core material that is a conductor.

Further, in this mode, the piezoelectric substrate has the same structure as an internal structure (an inner conductor and a dielectric) included in a coaxial cable; therefore, the piezoelectric substrate of this mode can provide a structure that exhibits high electromagnetic shielding performance and is strong against noise when applied to a coaxial cable.

The conductor is preferably an electrically good conductor, and examples thereof include a copper wire, an aluminum wire, an SUS wire, a metal wire covered with an insulating film, a carbon fiber, a resin fiber integrated with a carbon fiber, a tinsel wire, and an organic electroconductive material.

The term "tinsel wire" used herein refers to a fiber on which a copper foil is spirally wound.

Among these conductors, from the standpoints of improving the piezoelectric sensitivity and imparting the piezoelectric substrate with high bendability, a tinsel wire and a carbon fiber are preferred.

Particularly, in those applications where low electrical resistance as well as bendability and flexibility are required, it is preferred to use a tinsel wire.

As for the form of the tinsel wire, the tinsel wire has a structure in which a copper foil is helically wound around a fiber, and the use of copper having a high electroconductivity enables to reduce the output impedance. Therefore, by using such a tinsel wire as the core material, the piezoelectricity of the piezoelectric substrate is further improved.

In those applications where very high bendability and ductility are required and the piezoelectric substrate is processed into a woven fabric, a knitted fabric or the like (e.g., piezoelectric woven fabrics, piezoelectric knitted fabrics, and piezoelectric sensors (woven fabric-like piezoelectric sensors and knitted fabric-like piezoelectric sensors)), it is preferred to use a carbon fiber.

Further, in cases where the piezoelectric substrate is used as a fiber to produce a piezoelectric woven fabric or a piezoelectric knitted fabric, ductility and high bendability are required. In such applications, a yarn-form or fiber-form signal line conductor is preferred. A piezoelectric substrate including a yarn-form or fiber-form signal line conductor is highly bendable and thus suitable for processing using a weaving machine or a knitting machine.

When the piezoelectric substrate includes a core material that is a conductor, it is preferred that the piezoelectric substrate includes an outer conductor on an outer peripheral side of the elongate piezoelectric body that is helically wound around the core material, and that the core material that is a conductor and the outer conductor are electrically insulated from each other.

In this mode, since the inside of the piezoelectric substrate (the piezoelectric body and the core material that is a conductor) can be electrostatically shielded by the outer conductor, a change in the voltage or charge of the core material that is a conductor, which is caused by static electricity outside the piezoelectric substrate, is suppressed.

Therefore, the piezoelectric substrate can attain more stable piezoelectricity.

The outer conductor is preferably connected to a ground potential.

The material of the outer conductor is not particularly restricted, and examples thereof mainly include the following materials based on cross-sectional shapes.

For example, as the material of the outer conductor having a rectangular cross-section, a copper foil ribbon obtained by rolling and processing a copper wire having a circular cross-section into a flat plate form, an Al foil ribbon or the like can be used.

For example, as the material of the outer conductor having a circular cross-section, a copper wire, an aluminum wire, an SUS wire, a metal wire covered with an insulating film, a carbon fiber, a resin fiber integrated with a carbon fiber, a tinsel wire or the like can be used.

Further, as the material of the outer conductor, an organic electroconductive material coated with an insulating material may be used as well.

The outer conductor is preferably arranged to wrap the core material that is a conductor and the piezoelectric body such that a short circuit does not occur between the outer conductor and the core material that is a conductor.

As a method of wrapping the core material that is a conductor and the piezoelectric body, for example, a method of wrapping them by helically winding a copper foil or the like thereon, or a method of processing a copper wire or the like into a cylindrical braid and then wrapping the core material and the piezoelectric body in this braid, can be selected.

The wrapping method is, however, not restricted to the above-described methods.

By wrapping the core material that is a conductor and the piezoelectric body, the electrostatic shielding effect can be further improved.

As for the arrangement of the outer conductor, it is also a preferred form to arrange the outer conductor in such a manner to envelop a minimum basic structural unit (i.e., the conductor and the piezoelectric body) of the piezoelectric substrate of the first mode in a cylindrical shape.

Moreover, for example, in cases where the below-described piezoelectric knitted fabric or piezoelectric woven fabric is processed into a sheet form with the use of the piezoelectric substrate including the minimum basic structural unit, it is also a preferred form to arrange a planar or sheet-form conductor in close proximity on one of or both of the opposing surfaces of the processed fabric.

As the cross-sectional shape of the outer conductor, various cross-sectional shapes, such as a circular shape, an elliptical shape, a rectangular shape or an irregular shape, can be adopted. Particularly, a rectangular cross-section can be planarly and tightly adhered to the conductor, the piezoelectric body and the like; therefore, it enables to efficiently detect a charge generated by a piezoelectric effect as a voltage signal.

(Piezoelectric Substrate of Second Mode)

The piezoelectric substrate of the second mode does not include a core material.

In the piezoelectric substrate of the second mode, the elongate piezoelectric body is helically wound around an imaginary helical axis. The imaginary helical axis is, in other words, a central axis of a helical structure formed by the piezoelectric body.

The piezoelectric substrate of the second mode that does not include a core material is advantageous in terms of bendability and flexibility (ductility). Further, this piezoelectric substrate is more advantageous in terms of resistance to repeated deformation (i.e., avoidance of fatigue fracture of a metal wire) as compared to a mode in which the piezoelectric substrate includes a core material that is a metal wire.

The piezoelectric substrate of the second mode may take, for example, a mode in which a space (gap) is absent or substantially absent around the helical axis in the helical structure formed by the piezoelectric body, or a mode in which a prescribed space exists around the helical axis.

Examples of a method of adjusting the size of the space around the helical axis include: a method of adjusting the winding process of the piezoelectric body; a method of winding the piezoelectric body around a fiber that is dissolved by a specific action (e.g., a water-soluble fiber) and subsequently allowing the fiber to dissolve with time, or dissolving and thereby removing the fiber with water; and a method of winding the piezoelectric body around a core material and subsequently removing the core material. It is noted here that the major axis diameter of the fiber or that of the core material can be selected as appropriate in accordance with the mode of the space.

<Insulator>

The piezoelectric substrate may also include an insulator on the outermost periphery (e.g., in cases where the piezoelectric substrate includes an outer conductor, on an outer peripheral side than the outer conductor).

When the piezoelectric substrate includes an insulator on the outermost periphery, entry of a liquid (e.g., water or sweat), dust or the like from the outside can be inhibited. As a result, the durability of the piezoelectric substrate is further improved.

The insulator is not particularly restricted, and examples thereof include vinyl chloride resins, polyethylene resins, polypropylene resins, ethylene-tetrafluoroethylene copolymers (ETFE), tetrafluoroethylene-hexafluoropropylene copolymers (FEP), tetrafluoroethylene resins (PTFE), tetrafluoroethylene-perfluoropropylvinyl ether copolymers (PFA), fluororubbers, polyester resins, polyimide resins, polyamide resins, polyethylene terephthalate resins (PET), and rubbers (including elastomers).

Examples of a method of arranging the insulator on the outermost periphery of the piezoelectric substrate include:

a method of winding an elongate insulator on the piezoelectric substrate on which the insulator is not yet arranged;

a method of arranging the piezoelectric substrate, on which the insulator is not yet arranged, in the interior space of a cylindrical insulator (e.g., a heat-shrinkable tube) and subsequently allowing the cylindrical insulator to shrink with heat and tightly adhere to the piezoelectric substrate:

a method of coating the piezoelectric substrate with an insulating molten resin and subsequently allowing the resin to cool and solidify; and a method of coating the piezoelectric substrate with an insulating resin coating liquid and subsequently allowing the liquid to solidify.

<Adhesive>

The piezoelectric substrate may include an adhesive as well.

In a mode in which the piezoelectric substrate includes an adhesive, at least the piezoelectric body that is helically wound can be mechanically integrated.

Further, when the piezoelectric substrate includes a member(s) other than the piezoelectric body (e.g., a core material, an outer conductor and/or the like), the piezoelectric body and the member(s) other than the piezoelectric body can be integrated by the adhesive.

By mechanically integrating the piezoelectric body (or the piezoelectric body and the member(s) other than the piezoelectric body), when a force is applied to the piezoelectric substrate, the force is more likely to act on the piezoelectric body of the piezoelectric substrate. Therefore, the piezoelectricity is further improved.

Examples of the adhesive material include epoxy-based adhesives, urethane-based adhesives, vinyl acetate resin-based emulsion-type adhesives, EVA-based emulsion-type adhesives, acryl resin-based emulsion-type adhesives, styrene-butadiene rubber-based latex-type adhesives, silicone resin-based adhesives, α-olefin (isobutene-maleic anhydride resin)-based adhesives, vinyl chloride resin-based solvent-type adhesives, rubber-based adhesives, elastic adhesives, chloroprene rubber-based solvent-type adhesives, nitrile rubber-based solvent-type adhesives, and cyanoacrylate-based adhesives.

<Other Elements>

The piezoelectric substrate may also include an element(s) other than the above-described ones.

Examples of other elements include fibers other than the elongate piezoelectric body.

In the piezoelectric substrate, the elongate piezoelectric body may be wound along with a fiber other than the elongate piezoelectric body.

When a core material that is a conductor is used in the piezoelectric substrate of the first mode, an insulating layer may be arranged between the core material that is a conductor and the piezoelectric body.

Further, any known extraction electrode can be bonded to the piezoelectric substrate. Examples of the extraction electrode include electrode components, such as connectors, and crimp terminals. An electrode component can be bonded to the piezoelectric substrate by, for example, brazing such as soldering, or using an electroconductive bonding agent.

Specific examples of the piezoelectric substrate will now be described referring to the drawings; however, the piezoelectric substrate of the disclosure is not restricted to the following specific examples.

It is noted here that, in all of the drawings, substantially the same elements are assigned with the same symbols, and redundant descriptions may be omitted.

Specific Example A

Figure 1B:
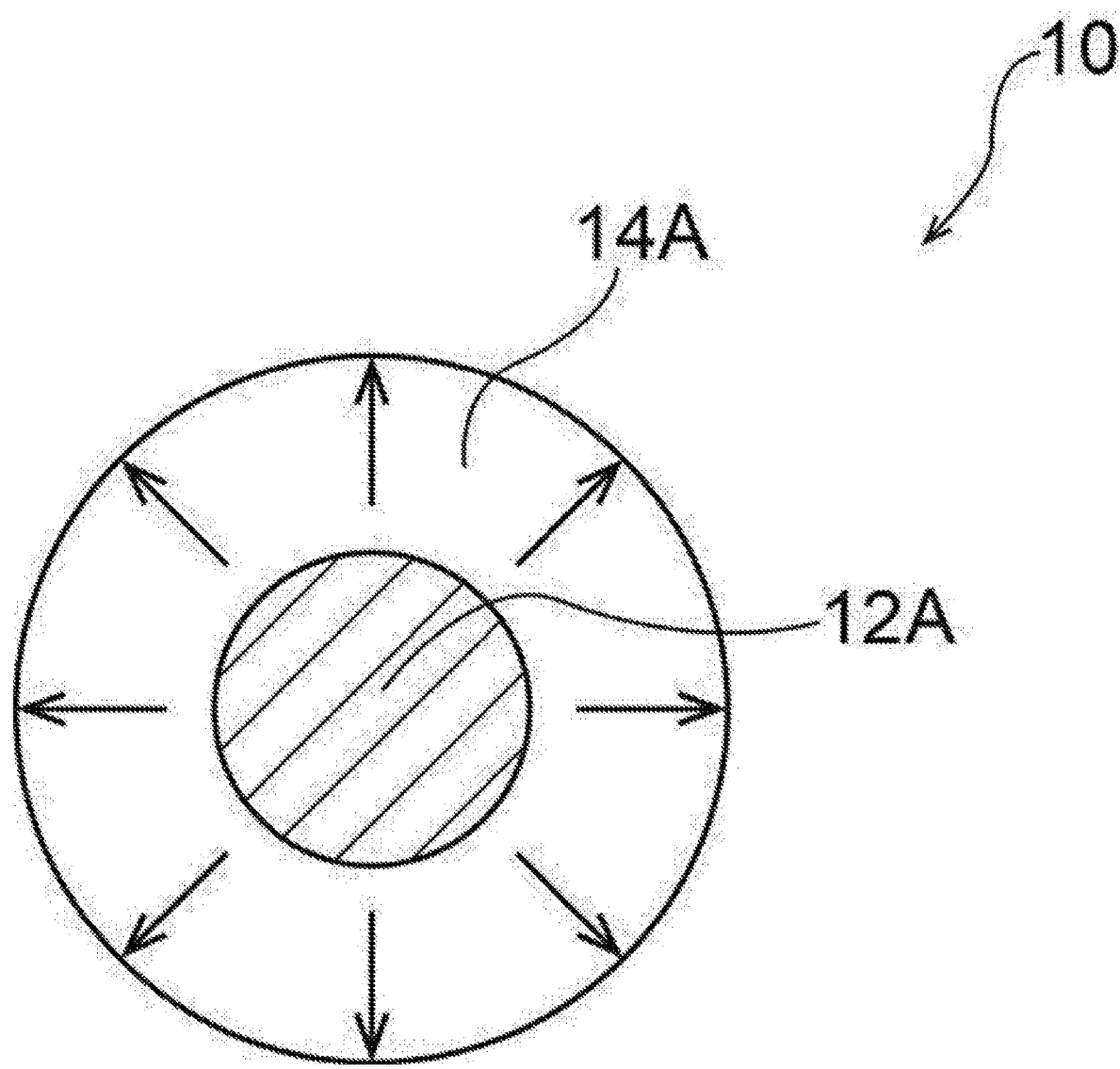
FIG. 1B is a cross-sectional view taken along a line X-X' of FIG. 1A.

FIG. 1A is a side view schematically illustrating a piezoelectric substrate according to a specific example A, and FIG. 1B is a cross-sectional view taken along a line X-X' of FIG. 1A.

The specific example A is a specific example of the piezoelectric substrate of the first mode (piezoelectric substrate including a core material) that does not include any outer conductor.

As illustrated in FIG. 1A, a piezoelectric substrate 10 which is the specific example A includes: an elongate core material 12A which is a non-conductor; and an elongate piezoelectric body 14A. The piezoelectric body 14A is helically wound in a single direction with no gap along the outer peripheral surface of the core material 12A from one end to the other end at a helix angle β1.

The helix angle β1 is, in the side view, an angle formed by the direction of a helical axis G1 (the axial direction of the core material 12A in this example) and the length direction of the piezoelectric body 14A.

In this piezoelectric substrate 10, the piezoelectric body 14A is wound in a left-handed manner on the core material 12A. Specifically, when the piezoelectric substrate 10 is viewed from one end of the axial direction of the core material 12A (from right-end side of FIG. 1A), the piezoelectric body 14A is wound in a left-handed manner from the front side toward the back side of the core material 12A.

Further, in FIG. 1A, the main orientation direction of the optically active polypeptide included in the piezoelectric body 14A is indicated by a double-headed arrow E1. In other words, the main orientation direction of the optically active polypeptide and the length direction of the piezoelectric body 14A are substantially parallel to each other.

In the piezoelectric substrate 10, the members (the core material 12A and the piezoelectric body 14A) may be integrated (immobilized) with each other by impregnation of an adhesive (not illustrated) between the members.

The actions and effects of the piezoelectric substrate 10 are described below.

For example, when a tension is applied in the length direction of the piezoelectric substrate 10, a shear stress is added to the optically active polypeptide included in the piezoelectric body 14A, and the optically active polypeptide is polarized. This polarization of the optically active polypeptide is believed to be caused by phase alignment in the radial direction of the piezoelectric substrate 10 as illustrated by arrows in FIG. 1B. As a result, the piezoelectricity of the piezoelectric substrate 10 is expressed.

Specific Example B

Figure 2:
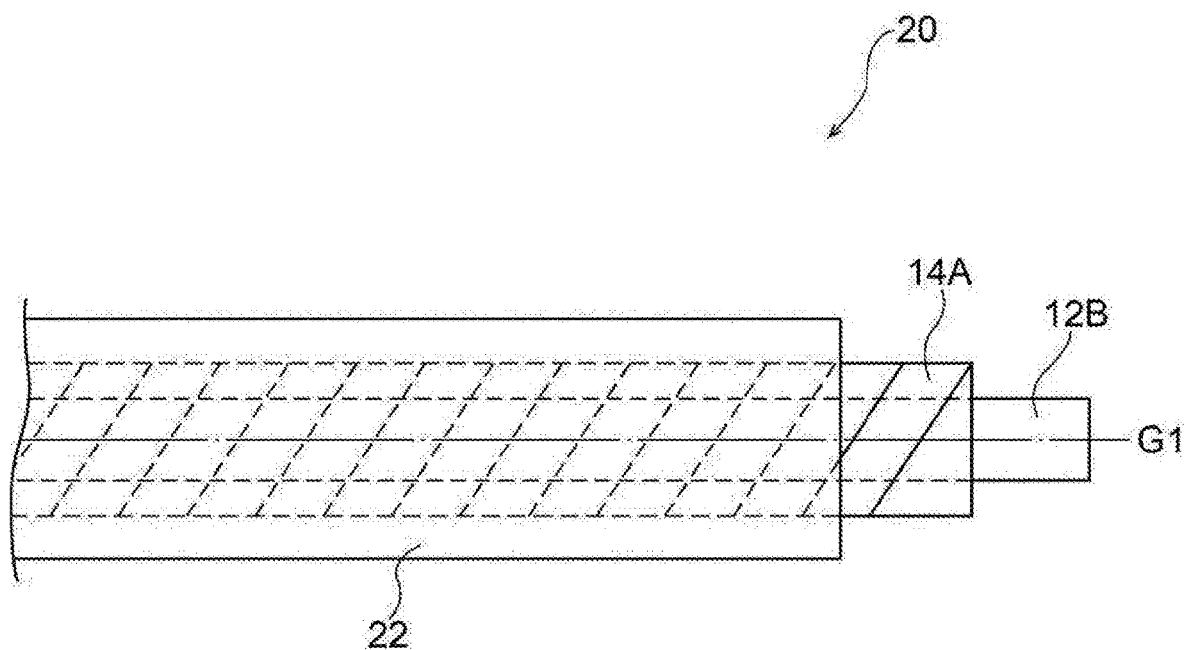
FIG. 2 is a side view schematically illustrating a piezoelectric substrate according to another specific example of the first mode.

FIG. 2 is a side view schematically illustrating a piezoelectric substrate according to a specific example B.

The specific example B is a specific example of the piezoelectric substrate of the first mode (piezoelectric substrate including a core material) that includes an outer conductor.

As illustrated in FIG. 2, a piezoelectric substrate 20 which is the specific example B is different from the piezoelectric substrate 10 of the specific example A in that: the elongate core material 12A, which is a non-conductor, is changed to an elongate core material 12B that is a conductor; and the piezoelectric substrate 20 includes an outer conductor 22 on an outer peripheral side of the piezoelectric body 14A, with the core material 12B and the outer conductor 22 being electrically insulated from each other. Other constitutions are the same as those of the piezoelectric substrate 10 of the specific example A.

Preferred modes of the outer conductor 22 are as described above. The outer conductor 22 is formed by, for example, helically winding a copper foil ribbon around the piezoelectric body 14A that is helically wound around the core material 12B.

In the piezoelectric substrate 20, the members (the core material 12B, the piezoelectric body 14A, and the outer conductor 22) may be integrated (immobilized) with one another by impregnation of an adhesive (not illustrated) between the members.

As illustrated in FIG. 2, when the piezoelectric substrate 20 is viewed from one side, an end of the wound body of the piezoelectric body 14A (i.e., the helically-wound piezoelectric body 14A) and an end of the outer conductor 22 are displaced from one another. This ensures insulation of the core material 12B and the outer conductor 22 from each other. It is noted here, however, that these ends are not necessarily required to be displaced from one another, and the positions of these ends may overlap with each other in a side view as long as the core material that is a conductor and the outer conductor are electrically insulated from each other.

In the piezoelectric substrate 20 as well, the same actions and effects are exerted as in piezoelectric substrate 10.

In addition, since the piezoelectric substrate 20 includes the core material 12B that is a conductor, an electrical signal (voltage signal or charge signal) generated in the piezoelectric body 14A can be more easily extracted via the core material 12B.

Moreover, since the piezoelectric substrate 20 includes the outer conductor 22, the inside of the piezoelectric substrate 20 (the piezoelectric body 14A and the core material 12B that is a conductor) can be electrostatically shielded by the outer conductor 22. Accordingly, a change in the voltage of the core material 12B caused by static electricity outside the piezoelectric substrate 20 can be suppressed, as a result of which more stable piezoelectricity can be attained.

The outer conductor 22 may be omitted in the piezoelectric substrate 20.

It is needless to say, however, that the actions and effects attributed to the core material 12B that is a conductor are exerted even when the outer conductor 22 is omitted.

Further, even if the outer conductor 22 is omitted, the piezoelectric substrate 20 has the same structure as an internal structure (an inner conductor and a dielectric) included in a coaxial cable; therefore, the piezoelectric substrate 20 can provide a structure that exhibits high electromagnetic shielding performance and is strong against noise when applied to a coaxial cable.

Specific Example C

Figure 3:
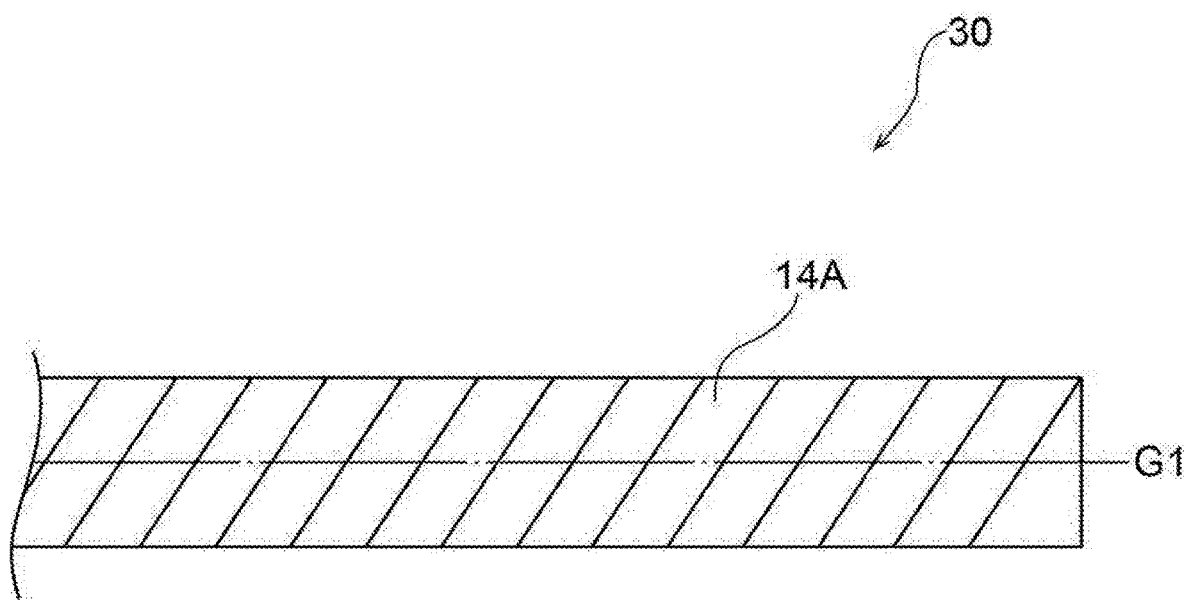
FIG. 3 is a side view schematically illustrating a piezoelectric substrate according to a specific example of a second mode.

FIG. 3 is a side view schematically illustrating a piezoelectric substrate according to a specific example C.

The specific example C is a specific example of the piezoelectric substrate of the second mode (piezoelectric substrate including no core material).

As illustrated in FIG. 3, a piezoelectric substrate 30 which is the specific example C is different from the piezoelectric substrate 10 of the specific example A in that: the elongate core material 12A, which is a non-conductor, is omitted (i.e., the piezoelectric body 14A is wound around the imaginary helical axis G1). Other constitutions are the same as those of the piezoelectric substrate 10 of the specific example A.

In the piezoelectric substrate 30, the wound body of the piezoelectric body 14A (i.e., the helically-wound piezoelectric body 14A) may be integrated (immobilized) by impregnation of an adhesive (not illustrated) between adjacent edges of the piezoelectric body 14A in the wound body of the piezoelectric body 14A.

As described above, in the piezoelectric substrate 30, a space (gap) may be present or absent around the helical axis of the helical structure formed by the piezoelectric body 14A.

In the piezoelectric substrate 30 as well, the same actions and effects are exerted as in piezoelectric substrate 10.

In addition, since the piezoelectric substrate 30 does not include any core material, the piezoelectric substrate 30 is advantageous in terms of bendability and flexibility (ductility).

Moreover, since the piezoelectric substrate 30 does not include a core material, the piezoelectric substrate 30 is more advantageous in terms of resistance against repeated deformation (i.e., avoidance of fatigue fracture of a metal wire) as compared to a mode including a core material that is a metal wire.

Specific Example D

Figure 4:
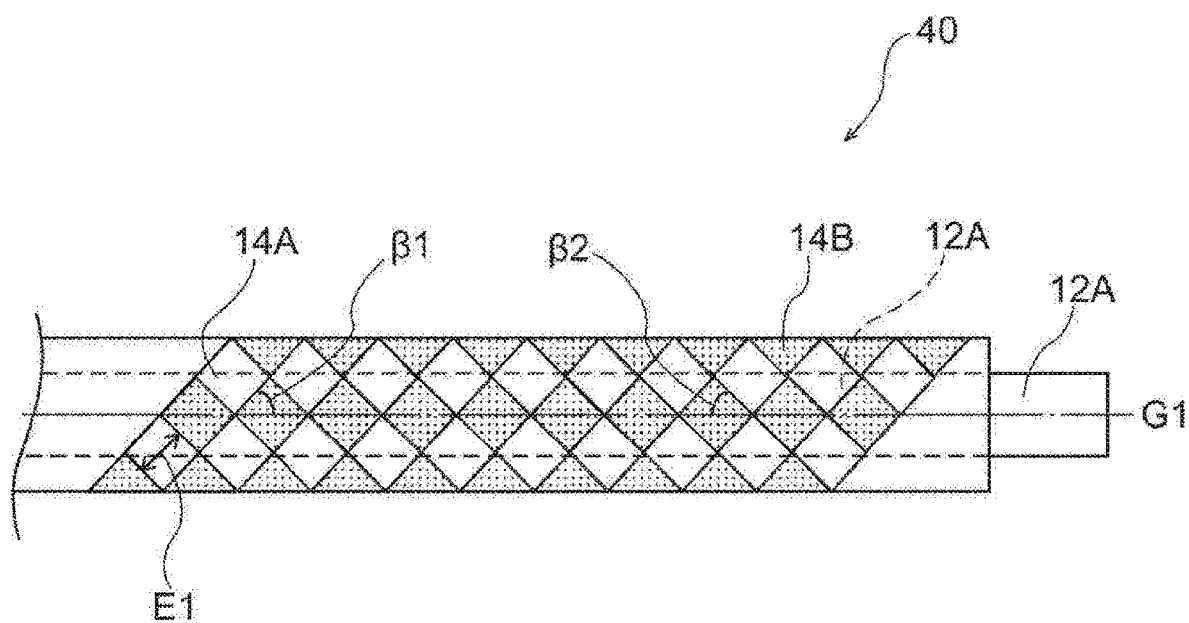
FIG. 4 is a side view schematically illustrating a piezoelectric substrate according to yet another specific example of the first mode.

FIG. 4 is a side view schematically illustrating a piezoelectric substrate according to a specific example D.

The specific example D is a specific example of the piezoelectric substrate of the first mode (piezoelectric substrate including a core material) in which the piezoelectric body and a fiber other than the piezoelectric body alternately intersect with each other to form a braided structure.

As illustrated in FIG. 4, a piezoelectric substrate 40 which is the specific example D includes: the elongate core material 12A; the elongate piezoelectric body 14A; and a fiber 14B other than the piezoelectric body. The piezoelectric body 14A is helically wound in a single direction with no gap along the outer peripheral surface of the core material 12A from one end to the other end at a helix angle β1. Further, the fiber 14B is helically wound in a direction different from the winding direction of the piezoelectric body 14A, with no gap along the outer peripheral surface of the core material 12A from one end to the other end at a helix angle β2. As illustrated in FIG. 4, the piezoelectric body 14A and the fiber 14B form a braided structure. The core material may be a conductor or a non-conductor.

In other words, the piezoelectric substrate 40, which is the specific example D, has a braided structure in which the piezoelectric body 14A and the fiber 14B alternately intersect with each other.

As illustrated in FIG. 4, in the piezoelectric substrate 40 of the specific example D, the piezoelectric body 14A is helically wound in a left-handed manner at a helix angle β1 while the fiber 14B is helically wound in a right-handed manner at a helix angle β2 with respect to the helical axis G1 of the core material 12A, and the piezoelectric body 14A and the fiber 14B alternately intersect with each other.

It is noted here that, in a side view, the helix angle β1 is an angle formed by the direction of the helical axis G1 (the axial direction of the core material 12A in this example) and the length direction of the piezoelectric body 14A, and the helix angle β2 is an angle formed by the direction of the helical axis G1 and the length direction of the fiber 14B.

Further, in FIG. 4, the main orientation direction of the optically active polypeptide included in the piezoelectric body 14A is indicated by a double-headed arrow E1. In other words, the main orientation direction of the optically active polypeptide and the length direction of the piezoelectric body 14A are substantially parallel to each other.

In the piezoelectric substrate 40, the members (the core material 12A, the piezoelectric body 14A, and the fiber 14B) may be integrated (immobilized) with one another by impregnation of an adhesive (not illustrated) between the members.

In the piezoelectric substrate 40 as well, the same actions and effects are exerted as in piezoelectric substrate 10.

In addition, since the piezoelectric substrate 40 has a braided structure, the piezoelectric substrate 40 is advantageous in terms of durability (e.g., the ease of maintaining the helically wound state of the piezoelectric body 14A).

<Applications of Piezoelectric Substrate>

Applications of the piezoelectric substrate of the disclosure are not particularly restricted.

Examples of an application of the piezoelectric substrate include force sensors, pressure sensors, displacement sensors, deformation sensors, motion sensors, vibration sensors, impact sensors, ultrasonic sensors, actuators, and energy harvesters.

Examples of the force sensors include sitting sensors; ball-hitting acceleration sensors and impact sensors for various ball-game sporting equipments, such as rackets, golf clubs, and bats; touch/impact sensors of stuffed toys; bed watching sensors; and security sensors for glasses and window frames;

Examples of the motion sensors include wearable motion sensors obtained by arranging the piezoelectric substrate on healthcare-related articles (e.g., various clothing items, such as T-shirts, sportswear, leggings, and socks; supporters; plaster casts; diapers; seats of infant push carts; wheelchair seats; medical incubator mats; shoes; shoe insoles; and watches).

Examples of the actuators include sheet transfer devices.

Examples of the energy harvesters include power generation wears and power generation shoes.

More specifically, the piezoelectric substrate can be arranged in various articles, such as various clothing items (e.g., shirts, suits, blazers, blouses, coats, jackets, blousons, jumpers, vests, dresses, trousers, skirts, pants, underwear (e.g., slips, petticoats, camisoles, and brassieres), socks, gloves, Japanese clothes, obi material, gold brocades, cool feeling clothes, neckties, handkerchiefs, mufflers, scarfs, stoles, and eye masks), supporters (e.g., neck supporters, shoulder supporters, chest supporters, abdominal supporters, waist supporters, arm supporters, leg supporters, elbow supporters, knee supporters, wrist supporters, and ankle supporters), footwear (e.g., sneakers, boots, sandals, pumps, mules, slippers, ballet shoes, and kung-fu shoes), insoles, towels, rucksacks, headgears (e.g., hats, caps, caskets, hunting caps, ten-gallon hats, flop hats, sun visors, and berets), cap straps, helmets, helmet chin straps, headscarfs, belts, seat covers, sheets, floor cushions, cushions, quilts, quilt covers, blankets, pillows, pillow cases, sofas, chairs, desks, tables, seats, seating units, toilet seats, massage chairs, beds, bed pads, carpets, baskets, masks, dressing bandages, ropes, stuffed toys, various nets, bathtubs, wall materials, window materials, window frames, personal computers and computer mice, and thereby used as a sensor, an actuator or an energy harvester.

Examples of an arrangement method include various methods, such as a method of sewing the piezoelectric substrate into an object of interest, a method of sandwiching the piezoelectric substrate between objects of interest, and a method of immobilizing the piezoelectric substrate with an object of interest using an adhesive.

Among the above-described applications, the piezoelectric substrate is preferably utilized in a sensor application or an actuator application.

Further, the piezoelectric substrate can be utilized as a switch that can switch a field effect transistor (FET) by applying a voltage generated by a stress to between the gate and source of the FET and is thus capable of switching ON-OFF in response to the stress.

The piezoelectric substrate can also be used for applications other than the above-described ones.

Examples of such other applications include beddings for roll-over detection; carpets for motion detection; insoles for motion detection; chest bands for respiration detection; masks for respiration detection; arm bands for strain detection; leg bands for strain detection; seats for seating detection; and stuffed toys, stuffed toy-type social robots and the like that are capable of differentiating contact states. In the stuffed toys, stuffed toy-type social robots and the like that are capable of differentiating contact states, for example, changes in pressure are detected by a contact sensor locally arranged in the stuffed toys and the like, and human actions of, for example, "rubbing", "hitting" and "pulling" the stuffed toys and the like can be differentiated from one another.

It is noted here that applications of the below-described piezoelectric woven fabric and piezoelectric knitted fabric are also the same as those of the piezoelectric substrate.

Moreover, the piezoelectric substrate according to one embodiment has excellent durability and is thus particularly suitable for, for example, those applications that are mounted on vehicles or used outdoors.

[Sensor and Actuator]

A sensor according to one embodiment includes the above-described piezoelectric substrate.

The sensor has excellent durability since it includes the piezoelectric substrate.

An actuator according to one embodiment also includes the above-described piezoelectric substrate.

The actuator has excellent durability since it includes the piezoelectric substrate.

[Piezoelectric Woven Fabric]

The piezoelectric woven fabric according to one embodiment has a woven fabric structure.

The woven fabric structure is composed of warp and weft.

In the piezoelectric woven fabric, at least either of the warp and the weft includes the above-described piezoelectric substrate.

Accordingly, the piezoelectric woven fabric exhibits the same effects as the piezoelectric substrate.

It is noted here that the term "woven fabric" used herein generally refers to a fabric that is processed into a film form by interlacing yarns to form a woven fabric structure. The term "piezoelectric woven fabric" used herein refers to, among such woven fabrics, one in which a piezoelectric effect is exerted by an outer stimulus (e.g., a physical force).

In the piezoelectric woven fabric according to one embodiment, both the warp and the weft may include the piezoelectric substrate.

In this mode, from the standpoint of improving the piezoelectric sensitivity and the piezoelectric output stability, it is preferred that the winding direction of the piezoelectric body included in the warp and the winding direction of the piezoelectric body included in the weft are different from each other, and that the chirality of the optically active polypeptide included in the warp and the chirality of the optically active polypeptide included in the weft are the same.

Or, it is preferred that the winding direction of the piezoelectric body included in the warp and the winding direction of the piezoelectric body included in the weft are the same, and that the chirality of the optically active polypeptide included in the warp and the chirality of the optically active polypeptide included in the weft are different from each other.

Examples of the yarns include polymer-containing yarns.

Examples of the polymer in the polymer-containing yarns include common polymers, such as polyesters and polyolefins.

The concept of the polymer-containing yarns also encompasses the above-described piezoelectric substrate.

The woven fabric structure of the piezoelectric woven fabric is not particularly restricted.

Examples of the woven fabric structure include basic structures, such as plain weave, twill weave, and satin weave.

The piezoelectric substrate may be used as the warp or the weft in the piezoelectric woven fabric, or may be used as a part of the warp or a part of the weft.

The piezoelectric woven fabric according to one embodiment may be a woven fabric having a three-dimensional structure. The phrase "woven fabric having a three-dimensional structure" used herein refers to a woven fabric that is sterically processed by additionally weaving yarns (warp and weft) in the thickness direction of a woven fabric having a two-dimensional structure.

Examples of such a woven fabric having a three-dimensional structure are described in, for example, Japanese National-Phase Publication (JP-A) No. 2001-513855.

The piezoelectric woven fabric according to one embodiment may take any configuration as long as at least some of the yarns constituting the woven fabric structure are constituted by the above-described piezoelectric substrate.

[Piezoelectric Knitted Fabric]

The piezoelectric knitted fabric according to one embodiment has a knitted fabric structure. The knitted fabric structure includes the above-described piezoelectric substrate.

Accordingly, the piezoelectric knitted fabric exhibits the same effects as the piezoelectric substrate.

The term "knitted fabric" used herein generally refers to a fabric that is produced by knitting yarns together while making loops. The term "piezoelectric knitted fabric" used herein refers to, among such knitted fabrics, one in which a piezoelectric effect is exerted by an outer stimulus (e.g., a physical force).

Examples of the yarns include polymer-containing yarns.

Examples of the polymer in the polymer-containing yarns include common polymers, such as polyesters and polyolefins.

The concept of the polymer-containing yarns also encompasses the above-described piezoelectric substrate.

The knitted fabric structure of the piezoelectric knitted fabric is not particularly restricted.

Examples of the knitted fabric structure include basic structures, such as weft knitting (flat knitting) and warp knitting (stitch bonding). Examples of weft knitting include plain knitting, rib knitting, double knitting, purl knitting, and circular knitting. Examples of warp knitting include basic structures, such as tricot knitting, atlas knitting, diamond knitting, and Milanese knitting.

The piezoelectric substrate may be used as a yarn in the piezoelectric knitted fabric, or as a part of the yarn.

The piezoelectric knitted fabric according to one embodiment may be a knitted fabric having a three-dimensional structure. The phrase "knitted fabric having a three-dimensional structure" used herein refers to a knitted fabric that is sterically processed by additionally knitting a yarn in the thickness direction of a knitted fabric having a two-dimensional structure.

The piezoelectric knitted fabric according to one embodiment may take any configuration as long as at least some of the yarns constituting the knitted fabric structure are constituted by the above-described piezoelectric substrate.

[Piezoelectric Device]

The piezoelectric device according to one embodiment includes: the above-described piezoelectric woven fabric; and an outer conductor for piezoelectric device, which is arranged at a position opposite to the principal surface of the woven fabric structure.

Alternatively, the piezoelectric device according to one embodiment includes: the above-described piezoelectric knitted fabric; and an outer conductor for piezoelectric device, which is arranged at a position opposite to the principal surface of the knitted fabric structure.

In other words, the piezoelectric device includes the piezoelectric woven fabric containing the piezoelectric substrate, or the piezoelectric knitted fabric containing the piezoelectric substrate.

Accordingly, the piezoelectric device exhibits the same effects as the piezoelectric substrate.

(Outer Conductor for Piezoelectric Device)

The outer conductor for piezoelectric device is preferably a ground conductor.

The material of the ground conductor is not particularly restricted, and examples thereof include the same materials as those of outer conductors that can be arranged in the above-described piezoelectric substrate.

A commonly-used electrode material can also be used as the outer conductor for piezoelectric device.

Examples of the electrode material include metals (e.g., Al), as well as Ag, Au, Cu, Ag—Pd alloys, Ag pastes, Cu pastes, carbon blacks, ITOs (crystallized ITO and amorphous ITO), ZnO, IGZO, IZO (registered trademark), electroconductive polymers (polythiophene and PEDOT), Ag nanowires, carbon nanotubes, and graphene (including materials in common with a first outer conductor).

The shape of the outer conductor for piezoelectric device is not particularly restricted, and it is preferably selected as appropriate in accordance with the intended purpose thereof.

It is preferred that the piezoelectric device according to one embodiment further includes an insulator for piezoelectric device between the outer conductor for piezoelectric device and the woven fabric structure or the knitted fabric structure.

This allows the piezoelectric device to have a constitution in which the occurrence of an electrical short circuit between a conductor (preferably, an inner conductor) and the outer conductor is likely to be suppressed.

(Insulator for Piezoelectric Device)

The insulator for piezoelectric device is not particularly restricted, and examples thereof include those materials exemplified above for insulators that can be arranged in the piezoelectric substrate.

The shape of the insulator for piezoelectric device is not particularly restricted, and it is preferably selected as appropriate in accordance with the intended purpose thereof.

[Biological Information Acquisition Device]

The piezoelectric substrate, the piezoelectric woven fabric, and the piezoelectric knitted fabric are also preferably used in biological information acquisition devices.

In other words, the biological information acquisition device according to one embodiment includes the piezoelectric substrate, the piezoelectric woven fabric, or the piezoelectric knitted fabric.

The biological information acquisition device is a device for acquiring biological information of a tested person or animal (hereinafter, collectively referred to as "test subject") by detecting a biological signal of the test subject using the piezoelectric substrate, the piezoelectric woven fabric, or the piezoelectric knitted fabric.

Examples of the biological signal include a pulse wave signal (heart-rate signal), a respiration signal, a motion signal, a cardiac action, and a body tremor.

The term "body tremor" used herein refers to a rhythmic involuntary movement of a body part (e.g., finger, hand, forearm, or upper limb).

The detection of the cardiac action also includes detection of an effect of a force exerted by the cardiac function of the body.

In other words, when the heart pumps blood to the aorta and the pulmonary artery, the body is subjected to a reaction force in the opposite direction of the blood flow. The strength and the direction of this reaction force vary with the functional stages of the heart. The reaction force is detected by sensing the cardiac actions on the outside of the body.

The biological information acquisition device is arranged in various articles, such as clothing items (e.g., shirts, suits, blazers, blouses, coats, jackets, blousons, jumper coats, vests, dresses, trousers, pants, underwear (e.g., slips, petticoats, camisoles, and brassieres), socks, gloves, Japanese clothes, obi materials, gold brocades, cool-feeling clothes, neckties, handkerchiefs, mufflers, scarfs, stoles, and eye masks), supporters (e.g., neck supporters, shoulder supporters, chest supporters, abdominal supporters, waist supporters, arm supporters, leg supporters, elbow supporters, knee supporters, wrist supporters, and ankle supporters), footwear (e.g., sneakers, boots, sandals, pumps, mules, slippers, ballet shoes, and kung-fu shoes), insoles, towels, rucksacks, headgears (e.g., hats, caps, caskets, hunting caps, ten-gallon hats, floppy hats, sun visors, and berets), helmets, helmet chin straps, headscarfs, belts, seat covers, sheets, floor cushions, cushions, quilts, quilt covers, blankets, pillows, pillow cases, sofas, chairs, desks, tables, seats, seating units, toilet seats, massage chairs, beds, bed pads, carpets, baskets, masks, dressing bandages, ropes, various nets, bathtubs, floor materials, wall materials, personal computers, and computer mice.

The articles to be provided with the biological information acquisition device are preferably those articles that are subjected to the body weight of a test subject, such as footwear, insoles, sheets, floor cushions, cushions, quilts, quilt covers, pillows, pillow cases, sofas, chairs, seats, seating units, toilet seats, beds, carpets, bathtubs, and floor materials. More specifically, the articles are preferably, for example, seats, seating sections, wheels, infant fall prevention stoppers and the like of infant push carts; seats, seating sections and the like of wheelchairs; and mats of medical incubators.

One example of the actions of the biological information acquisition device will now be described.

The biological information acquisition device is arranged on, for example, a bed or the seating surface of a chair. A test subject lies, sits or stands on this biological information acquisition device. In this state, when a tension is applied to the piezoelectric substrate, piezoelectric woven fabric or piezoelectric knitted fabric of the biological information acquisition device due to a biological signal generated by the test subject (e.g., body motion, periodic vibration (e.g., pulse or respiration), or change in the heart rate caused by a human emotion, such as a sense of "cuteness" or "fear"), polarization occurs in the optically active polypeptide included in the piezoelectric substrate, piezoelectric woven fabric or piezoelectric knitted fabric, as a result of which an electrical potential proportional to the tension is generated. This electrical potential changes over time in accordance with the biological signal generated by the test subject. For example, when the biological signal generated by the test subject is periodic vibration such as pulse or respiration, the electrical potential generated in the piezoelectric substrate, piezoelectric woven fabric or piezoelectric knitted fabric also changes periodically.

The time-dependent changes in the electrical potential generated in association with the application of a tension to the piezoelectric substrate, piezoelectric woven fabric or piezoelectric knitted fabric are acquired as voltage signals by a measurement module. The thus acquired time-dependent changes in the electrical potential (piezoelectric signal) form a composite wave of plural biological signals (pulse wave signals (heart-rate signals), respiration signals, and body motion signals). This composite wave is separated into signals of respective frequencies based on Fourier transformation, whereby separated signals are generated. These separated signals are each inverse-Fourier-transformed to obtain biological signals corresponding to the respective separated signals.

For example, when biological signals generated by a test subject form a composite wave of pulse signal and respiration signal, the electrical potential generated in association with the application of a tension to the piezoelectric substrate, piezoelectric woven fabric or piezoelectric knitted fabric of the biological information acquisition device changes periodically over time.

Humans generally have a pulse rate of from 50 to 90 beats per minute and a pulse frequency of from 0.6 to 3 Hz. Further, humans generally have a respiration rate of from 16 to 18 times per minute and a respiration frequency of from 0.1 to 1 Hz. Moreover, humans generally have a body motion frequency of 10 Hz or higher.

Based on these standards, the composite wave of plural biological signals can be separated into individual biological signals. For example, the composite wave can be separated into respiration signals and heart-rate signals. Further, velocity pulse wave signals can be obtained from the heart-rate signals. The separation of the composite wave of plural biological signals into individual biological signals is carried out by the above-described Fourier transformation and inverse Fourier transformation using, for example, a biological signal report program.

The composite wave of plural biological signals can be separated into each of the plural biological signals in the above-described manner.

Biological signal data may also be generated on the basis of at least one of the thus separated biological signals.

The biological signal data is not particularly restricted as long as it is calculated based on biological signals. Examples of such biological signal data include the number of biological signals per unit time, and the average number of past biological signals.

[Piezoelectric Fiber Structure]

The piezoelectric fiber structure of the third mode includes: a first piezoelectric substrate (hereinafter, also referred to as "piezoelectric substrate 3A") that is the above-described piezoelectric substrate; and a second piezoelectric substrate (hereinafter, also referred to as "piezoelectric substrate 3B") that is the above-described piezoelectric substrate in which the optically active polypeptide included in the piezoelectric body has the same chirality as the optically active polypeptide included in the piezoelectric body of the piezoelectric substrate 3A, and the winding direction of the piezoelectric body is opposite to that of the piezoelectric body in the piezoelectric substrate 3A.

In other words, the piezoelectric fiber structure of the third mode includes the piezoelectric substrate 3A and the piezoelectric substrate 3B. The piezoelectric substrate 3A and the piezoelectric substrate 3B both include an elongate piezoelectric body that is helically wound and includes an optically active polypeptide. The length direction of each piezoelectric body and the main orientation direction of each optically active polypeptide are substantially parallel, and each piezoelectric body has a degree of orientation F of from 0.50 to less than 1.00. Further, comparing the piezoelectric substrate 3A and the piezoelectric substrate 3B that are included in the piezoelectric fiber structure of the third mode, the optically active polypeptides included in the respective piezoelectric bodies have the same chirality, and the winding directions of the piezoelectric bodies are opposite to each other.

The piezoelectric fiber structure of the fourth mode includes: a first piezoelectric substrate (hereinafter, also referred to as "piezoelectric substrate 4A") that is the above-described piezoelectric substrate; and a second piezoelectric substrate (hereinafter, also referred to as "piezoelectric substrate 4B") that is the above-described piezoelectric substrate in which the optically active polypeptide included in the piezoelectric body has a chirality that is different from that of the optically active polypeptide included in the piezoelectric body of the piezoelectric substrate 4A, and the winding direction of the piezoelectric body is the same as that of the piezoelectric body in the piezoelectric substrate 4A.

In other words, the piezoelectric fiber structure of the fourth mode includes the piezoelectric substrate 4A and the piezoelectric substrate 4B. The piezoelectric substrate 4A and the piezoelectric substrate 4B both include an elongate piezoelectric body that is helically wound and includes an optically active polypeptide. The length direction of each piezoelectric body and the main orientation direction of each optically active polypeptide are substantially parallel, and each piezoelectric body has a degree of orientation F of from 0.50 to less than 1.00. Further, comparing the piezoelectric substrate 4A and the piezoelectric substrate 4B that are included in the piezoelectric fiber structure of the fourth mode, the optically active polypeptides included in the respective piezoelectric bodies have different chiralities, and the winding directions of the piezoelectric bodies are the same.

Hereinafter, the piezoelectric substrate 3A and the piezoelectric substrate 4A may be generally referred to as "piezoelectric substrate (A)", and the piezoelectric substrate 3B and the piezoelectric substrate 4B may be generally referred to as "piezoelectric substrate (B)".

In other words, the piezoelectric fiber structure of the third mode or the fourth mode includes: the piezoelectric substrate (A); and the piezoelectric substrate (B) in which the optically active polypeptide included in the piezoelectric body has the same chirality as the optically active polypeptide included in the piezoelectric body of the piezoelectric substrate (A), and the winding direction of the piezoelectric body is opposite to that of the piezoelectric body of the piezoelectric substrate (A), or in which the optically active polypeptide included in the piezoelectric body has a chirality that is different from that of the optically active polypeptide included in the piezoelectric body of the piezoelectric substrate (A), and the winding direction of the piezoelectric body is the same as that of the piezoelectric body of the piezoelectric substrate (A).

Each of the piezoelectric substrate (A) and the piezoelectric substrate (B) may independently include a core material or no core material. In other words, each of the piezoelectric substrate (A) and the piezoelectric substrate (B) may independently be a pressure substrate of the first mode or a pressure substrate of the second mode.

When the piezoelectric substrate is a pressure substrate including no core material (i.e., the pressure substrate of the second mode), the substrate can be produced by, for example, twisting or crimping an elongate piezoelectric body containing an optically active polypeptide into a state of being helically wound around an imaginary helical axis.

Meanwhile, when the pressure substrate is a substrate including a core material (i.e., the pressure substrate of the first mode), the substrate can be produced by covering the core material with an elongate piezoelectric body containing an optically active polypeptide.

The above-described piezoelectric fiber structures have excellent antibacterial performance. The effects thereof are presumed as follows.

For example, when a tension is applied to the pressure fiber structure of the third mode, the surface of the piezoelectric substrate 3A is electrically charged and the surface of the piezoelectric substrate 3B is also electrically charged but with a potential opposite to that of the piezoelectric substrate 3A, as a result of which a strong electric field is generated at the interface between the piezoelectric substrate 3A and the piezoelectric substrate 3B. In cases where bacteria or the like exist in the thus generated strong electric field, since the cell membranes of the bacteria or the like are broken by the strong electric field, the piezoelectric fiber structure of the third mode exerts an antibacterial effect.

Similarly, when a tension is applied to the pressure fiber structure of the fourth mode, the surface of the piezoelectric substrate 4A and that of the piezoelectric substrate 4B are charged with opposite potentials and a strong electric field is thus generated at the interface between the piezoelectric substrate 4A and the piezoelectric substrate 4B, whereby an antibacterial effect is exerted.

As a piezoelectric fiber structure, from the productivity standpoint, the piezoelectric fiber structure of the third mode (i.e., a piezoelectric fiber structure wherein, in two piezoelectric substrates included therein, their optically active polypeptides have the same chirality and the winding directions of the piezoelectric bodies are opposite to one another) is preferred.

In the piezoelectric fiber structure of the third mode, either one of the piezoelectric substrate 3A and the piezoelectric substrate 3B is of an S-winding type in which, when viewed from one end of the central axis (helical axis) of the piezoelectric substrate (e.g., from the right-end side of FIG. 1A), the elongate piezoelectric body is wound in a left-handed (counterclockwise) manner from the front side toward the back side. Further, the other of the piezoelectric substrate 3A and the piezoelectric substrate 3B is of a Z-winding type in which, when viewed from one end of the central axis (helical axis) of the piezoelectric substrate (e.g., from the right-end side of FIG. 1A), the elongate piezoelectric body is wound in a right-handed (clockwise) manner from the front side toward the back side.

Meanwhile, in the piezoelectric fiber structure of the fourth mode, the piezoelectric bodies included in the piezoelectric substrate 4A and the piezoelectric substrate 4B may have the same winding direction, and the piezoelectric substrate 4A and the piezoelectric substrate 4B may both be of an S-winding type or a Z-winding type.

In these piezoelectric fiber structures, the piezoelectric substrate (A) and the piezoelectric substrate (B) may be twisted together or paralleled with each other.

Further, these piezoelectric fiber structures are not particularly restricted as long as they include the piezoelectric substrate (A) and the piezoelectric substrate (B) and, from the standpoint of the above-described antibacterial effect, examples thereof include those in which the piezoelectric substrate (A) and the piezoelectric substrate (B) are twisted together and those in which the piezoelectric substrate (A) and the piezoelectric substrate (B) are paralleled with each other, as well as those in which the piezoelectric substrate (A) and the piezoelectric substrate (B) alternately intersect with other to form a braided structure, woven fabric structures in which the piezoelectric substrate (A) and the piezoelectric substrate (B) are each used as a part of the warp or the weft, and knitted fabric structures in which the piezoelectric substrate (A) and the piezoelectric substrate (B) are knitted together.

Moreover, from the standpoint of increasing the adjoining region of the piezoelectric substrate (A) and the piezoelectric substrate (B), it is preferred that the piezoelectric fiber structures themselves have an elongate shape.

Examples of a piezoelectric fiber structure having an elongate shape include those in which the piezoelectric substrate (A) and the piezoelectric substrate (B) are twisted together or paralleled with each other, or alternately intersect to form a braided structure.

Thereamong, from the standpoint of antibacterial effect, a piezoelectric fiber structure in which the piezoelectric substrate (B) is arranged along the piezoelectric substrate (A) (e.g., a piezoelectric fiber structure in which the piezoelectric substrate (A) and the piezoelectric substrate (B) are twisted together or paralleled with each other) is preferred. Further, from the standpoints of durability and the like, a piezoelectric fiber structure in which the piezoelectric substrate (A) and the piezoelectric substrate (B) are twisted together is more preferred.

In the piezoelectric fiber structure in which the piezoelectric substrate (A) and the piezoelectric substrate (B) are twisted together, when viewed from one end of the central axis of the piezoelectric fiber structure (hereinafter, also referred to as "structural axis"), the winding direction of each piezoelectric substrate may be left-handed (i.e., S-winding) or right-handed (i.e., Z-winding) from the front side toward the back side.

It is noted here that FIG. 5 described below represents an example of the piezoelectric fiber structure of the third mode in which the piezoelectric substrate 3A and the piezoelectric substrate 3B are wound in a Z shape with respect to the structural axis.

It is preferred that the helix angle of the piezoelectric substrate (A) and that of the piezoelectric substrate (B) are substantially the same and, for example, the difference between their helix angles is within ±5°.

The terms "helix angle of the piezoelectric substrate (A)" and "helix angle of the piezoelectric substrate (B)" used herein each mean an angle with respect to the structural axis of the piezoelectric fiber structure. Further, the term "structural axis" used herein means, in a piezoelectric fiber structure in which the piezoelectric substrate (A) and the piezoelectric substrate (B) are helically wound, the central axis of a helical structure formed by the piezoelectric substrate (A) and the piezoelectric substrate (B).

Examples of a method of producing the piezoelectric fiber structure include a method of paralleling the piezoelectric substrate (A) and the piezoelectric substrate (B), and a method of winding the piezoelectric substrate (A) and the piezoelectric substrate (B) by twisting, crimping or the like.

The piezoelectric fiber structure according to one embodiment may have a constitution which further includes an elongate core material and in which the piezoelectric substrate (A) and the piezoelectric substrate (B) are helically wound on the elongate core material. The elongate core material may be, for example, a non-electroconductive core material or a conductor.

The material of the non-electroconductive core material is not particularly restricted as long as it is not electroconductive, and examples thereof include polymer resins, such as polyamide resins, polyester resins, acrylic resins, polyethylene resins, polypropylene resins, polyvinyl chloride resins, polysulfone resins, polyether resins, and polyurethane resins; cellulose-based resins; and inorganic materials, such as glass, silica gel, and ceramics. These materials may be used singly, or in combination of two or more kinds thereof.

As for the shape (elongate shape) of the non-electroconductive core material, the major axis diameter is not particularly restricted; however, the non-electroconductive core material is preferably a fiber-form core material composed of a single or plural bundles.

Examples of the fiber-form core material include yarns (monofilament yarns and multifilament yarns).

The conductor is preferably an electrically good conductor, and examples thereof include a copper wire, an aluminum wire, an SUS wire, a metal wire covered with an insulating film, a carbon fiber, a resin fiber integrated with a carbon fiber, a tinsel wire, and an organic electroconductive material. The term "tinsel wire" used herein refers to a fiber on which a copper foil is spirally wound. Among these conductors, from the standpoints of improving the piezoelectric sensitivity and the piezoelectric output stability and imparting the piezoelectric fiber structure with high bendability, a tinsel wire and a carbon fiber are preferred.

The piezoelectric fiber structure according to one embodiment is not required to include an elongate core material. When the piezoelectric fiber structure does not include any elongate core material, the piezoelectric fiber structure tends to have excellent bendability and flexibility (ductility) and, since the step of preparing the elongate core material is omitted, the production process of the piezoelectric fiber structure can be simplified.

<Specific Mode of Piezoelectric Fiber Structure>

As one example of the piezoelectric fiber structure, a specific mode of the above-described piezoelectric fiber structure of the third mode will now be described referring to a drawing.

Figure 5:
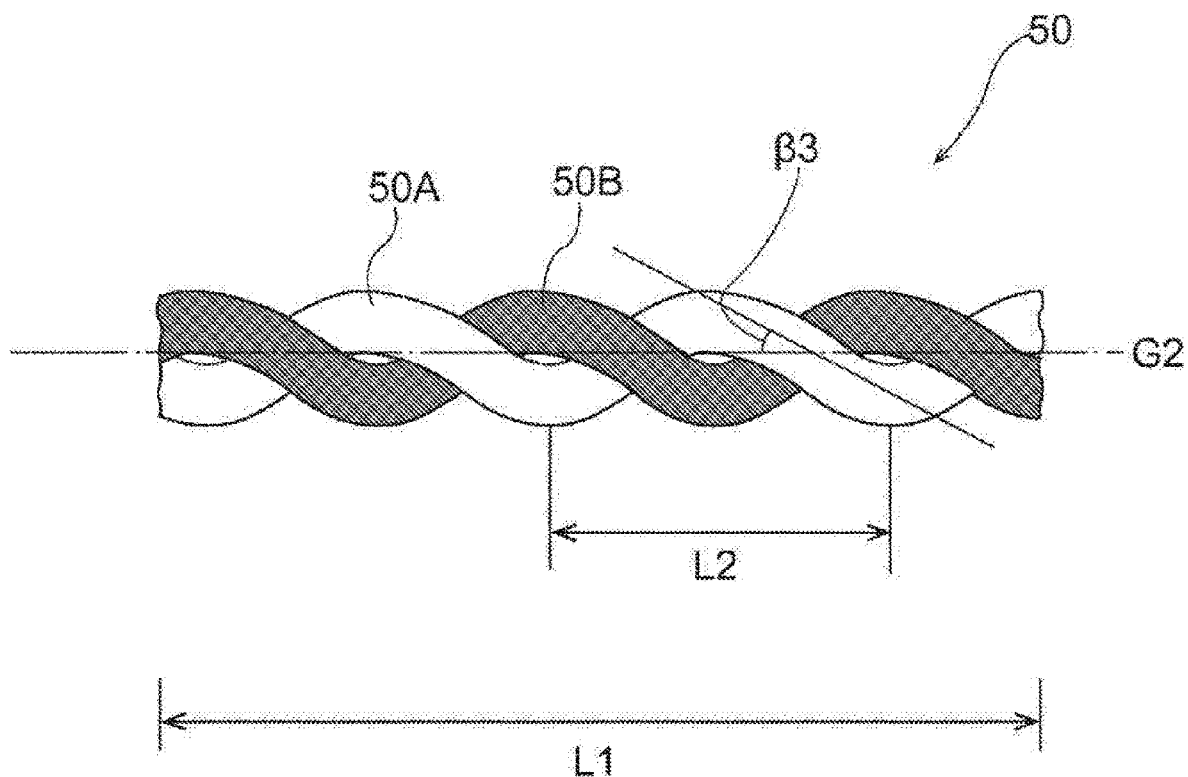
FIG. 5 is a side view schematically illustrating a piezoelectric fiber structure according to a specific example of a third mode.

As illustrated in FIG. 5, in a piezoelectric fiber structure 50 of this specific mode, a piezoelectric substrate 50A and a piezoelectric substrate 50B are twisted together about the same winding axis G2 at the same lap number. More specifically, in the piezoelectric fiber structure 50, the piezoelectric substrate 50A is helically wound in a right-handed manner with respect to the winding axis G2.

The phrase "wound in a right-handed manner" used herein means that, when the piezoelectric fiber structure 50 is viewed from one end in the direction of the winding axis G2 (from the right-end side in the case of FIG. 5), the piezoelectric substrate 50A is wound in a right-handed manner from the front side toward the back side of the winding axis G2.

In FIG. 5, the piezoelectric substrate 50B and the piezoelectric substrate 50A are twisted at a lap number of "3". In this case, in FIG. 5, the lap number per a length L1 of the piezoelectric fiber structure 50 is "3", and the distance of a single lap of the piezoelectric substrate 50A (which is synonymous with the distance of a single lap of the piezoelectric substrate 50B) is L2. Further, in FIG. 5, an angle formed by the winding axis G2 and the length direction (i.e., helix angle) of the piezoelectric substrate 50A is β3.

In the piezoelectric substrate 50A, an elongate piezoelectric body 54A is helically wound around an imaginary helical axis G1A. The piezoelectric body 54A includes an optically active polypeptide, a length direction of the piezoelectric body 54A and a main orientation direction of the optically active polypeptide are substantially parallel to each other, and the piezoelectric body has a degree of orientation F of from 0.50 to less than 1.00.

Similarly, in the piezoelectric substrate 50B, an elongate piezoelectric body 54B is helically wound around an imaginary helical axis G1B. Similarly to the piezoelectric body 54A, the piezoelectric body 54B includes an optically active polypeptide, a length direction of the piezoelectric body 54A and a main orientation direction of the optically active polypeptide are substantially parallel to each other, and the piezoelectric body has a degree of orientation F of from 0.50 to less than 1.00.

Further, the chirality of the optically active polypeptide included in the piezoelectric body 54A and that of the optically active polypeptide included in the piezoelectric body 54B are the same, and the winding direction of the piezoelectric body 54A and that of the piezoelectric body 54B are opposite to each other. Specifically, the piezoelectric substrate 50A is of an S-winding type (i.e., the piezoelectric body 54A is wound in an S shape around the helical axis G1A), while the piezoelectric substrate 50B is of a Z-winding type (i.e., the piezoelectric body 54B is wound in a Z shape around the helical axis G1B).

Examples of a combination of the winding directions of the piezoelectric bodies in the piezoelectric substrates (A) and (B) included in the piezoelectric fiber structure and the amino acids constituting the respective optically active polypeptides included in the piezoelectric bodies include those combinations shown in Table below.

In Table 1, "winding direction" indicates the winding direction of the piezoelectric body in each piezoelectric substrate, and "amino acid" means the amino acid constituting the optically active polypeptide included in the piezoelectric body of each piezoelectric substrate.

TABLE 1

| Piezoelectric fiber structure | Mode | Piezoelectric substrate | Winding direction | Amino acid |
|---|---|---|---|---|
| 1 | Third mode | Piezoelectric substrate 3A | S-winding type | L-amino acid |
|  |  | Piezoelectric substrate 3B | Z-winding type | L-amino acid |
| 2 | Third mode | Piezoelectric substrate 3A | S-winding type | D-amino acid |
|  |  | Piezoelectric substrate 3B | Z-winding type | D-amino acid |
| 3 | Fourth mode | Piezoelectric substrate 4A | S-winding type | L-amino acid |
|  |  | Piezoelectric substrate 4B | S-winding type | D-amino acid |
| 4 | Fourth mode | Piezoelectric substrate 4A | Z-winding type | L-amino acid |
|  |  | Piezoelectric substrate 4B | Z-winding type | D-amino acid |

The piezoelectric fiber structure having an elongate shape may be used as at least either the warp or the weft constituting the above-described piezoelectric woven fabric.

According to the piezoelectric woven fabric in which at least either the warp or the weft contains the piezoelectric fiber structure, the same effects as those of the piezoelectric fiber structure are exerted.

The piezoelectric woven fabric may include the piezoelectric fiber structure in both of the warp and the weft.

Moreover, the piezoelectric fiber structure having an elongate shape may be used as a yarn constituting the above-described piezoelectric knitted fabric.

According to the piezoelectric knitted fabric whose yarn includes the piezoelectric fiber structure, the same effects as those of the piezoelectric fiber structure are exerted.

EXAMPLES

The invention will now be described more concretely by way of examples thereof; however, the invention is not restricted to the following examples as long as they do not depart from the gist of the invention.

Example 1

<Preparation of Piezoelectric Body>

As a piezoelectric body, a raw silk (27-denier raw yarn) was prepared.

It is noted here that this raw silk was a long fiber composed of an optically active polypeptide. In addition, the raw silk (27-denier raw yarn) was a non-twisted yarn (number of twists=0 Tim) (see Table 2).

The 27-denier raw yarn had a thickness of from 0.06 to 0.04 mm.

(Measurement of Degree of Orientation F of Piezoelectric Body)

Using a wide-angle X-ray diffractometer (RINT 2550 manufactured by Rigaku Corporation, attached equipment: rotary sample table, X-ray source: CuKα, output: 40 kV, 370 mA, detector: scintillation counter), the above-described raw silk (piezoelectric body) was fixed on a holder, and the azimuthal distribution intensity of a crystal plane peak [2θ=20°] was measured.

In the thus obtained azimuthal distribution curve (X-ray interferogram), the degree of orientation F (C-axis orientation degree) of the raw silk (piezoelectric body) was calculated from a half width (α) of the peak using the following Formula (a):

$$\text{Degree of orientation } (F) = (180° - \alpha)/180° \tag{a}$$

In Formula (a), a represents the half width of the peak derived from orientation.

<Preparation of Piezoelectric Substrate (with Outer Conductor)>

As a core material that is a conductor, a tinsel wire "U24-01-00" manufactured by Meisei Industry Co., Ltd. (wire diameter: 0.26 mm, length: 200 mm) was prepared.

Crimp terminals were caulked to the respective ends of the core material to arrange electrical and mechanical connectors on the respective ends of the core material. In this process, the distance between the two crimp terminals was set at 150 mm.

Next, the raw silk (piezoelectric body) was helically wound around the core material with no gap such that the core material was not exposed.

The helix angle of the raw silk (i.e., the angle of the length direction of the raw silk with respect to the longitudinal direction of the core material) was set at 450, and the raw silk was wound in a left-handed direction (i.e., when viewed from one end of the core material, the raw silk was wound in a left-handed manner from the front side toward the back side).

Subsequently, as an outer conductor, a copper foil ribbon that had been slit-cut at a width of 0.6 mm was prepared. On the raw silk wound around the core material, this copper foil ribbon was wound with no gap such that the raw silk was not exposed. In this process, the helix angle and the winding direction of the copper foil ribbon were the same as the helix angle (45°) and the winding direction (left-handed winding) of the raw silk. The copper foil ribbon was wound in such a manner that it did not come into contact with the two crimp terminals.

Thereafter, as an adhesive, ARON ALPHA manufactured by Toagosei Co., Ltd. (cyanoacrylate-based adhesive) was dropped onto the resultant to impregnate the resultant with the adhesive, whereby the core material, the raw silk and the copper foil ribbon were bonded together and mechanically integrated.

A piezoelectric substrate was obtained in the above-described manner.

<Measurement of Piezoelectric Sensitivity of Piezoelectric Substrate (Electrometer)>

Using an electrometer, the piezoelectric sensitivity (pC/N·mm) of the thus obtained piezoelectric substrate was measured by the following method.

The result thereof is shown in Table 2.

—Method of Measuring Piezoelectric Sensitivity (pC/N·mm) of Piezoelectric Substrate (Electrometer)—

The piezoelectric substrate was chucked in a tensile tester (TENSILON RTG1250 manufactured by A&D Co., Ltd.) at a chuck distance of 150 mm. Specifically, the crimp terminal (electrical and mechanical connector) on one end of the piezoelectric substrate was chucked with one of the chuck members, and the crimp terminal (electrical and mechanical connector) on the other end of the piezoelectric substrate was chucked with the other chuck member. Further, the charge measuring electrodes of an electrometer (617 manufactured by Keithley Instruments, Inc.) were connected to the crimp terminals of the piezoelectric substrate, and the ground electrode of the electrometer (617 manufactured by Keithley Instruments, Inc.) was connected to the outer conductor (copper foil ribbon) of the piezoelectric substrate.

Subsequently, using the tensile tester, a tension in a triangular wave form was periodically and repeatedly applied to the piezoelectric substrate in a stress range of from 1 N to 2 N at a frequency of 0.2 Hz, and the amount of charge generated on the core material side of the piezoelectric body (raw silk) in this process was measured using the electrometer (617 manufactured by Keithley Instruments, Inc.).

The amount of generated charge per unit tensile force was calculated from the slope of a correlation straight line of a scatter diagram prepared by plotting the measured amount of generated charge Q [C] on the Y-axis and the tensile force of the piezoelectric substrate F [N] on the X-axis, and the thus calculated value was divided by the distance between the crimp terminals to determine the piezoelectric sensitivity (pC/N·mm).

<Evaluation of Moist Heat Resistance (Measurement of Sensitivity (pC/N mm) after Environmental Test)>

After measuring the initial piezoelectric sensitivity (pC/N·mm) in the above-described "Measurement of Piezoelectric Sensitivity of Piezoelectric Substrate (Electrometer)", a test piece of the piezoelectric substrate was hung and retained in a thermo-hygrostat incubator maintained at 85° C. and 85% RH for a prescribed period (192 hours). Then, for this test piece, the piezoelectric sensitivity (pC/N·mm) was determined in the same manner as the above-described "Method of Measuring Piezoelectric Sensitivity (pC/N-mm) of Piezoelectric Substrate (Electrometer)", and the thus obtained value was defined as "sensitivity after environmental test (pC/N·mm)". The result thereof is shown in Table 2.

It is noted here that, in Table 2, "-" indicates that the evaluation of the moist heat resistance was not performed.

Examples 2 to 6

The same operations as those of Example 1 were performed, except that the combination of the winding direction (left-handed winding or right-handed winding) and the helix angle of the raw silk was changed as shown in Table 2.

The results thereof are shown in Table 2.

Example 7

The same operations as those of Example 2 were performed, except that the raw silk (27-denier raw yarn) was changed to a refined silk.

The results thereof are shown in Table 2.

As the refined silk, one obtained by removing sericin from a raw silk (27-denier raw yarn) (multifilament: 88 denier; thickness=0.12 to 0.30 mm; number of twists=left 150 T/m) was used.

Examples 8 to 10

The same operations as those of Example 7 were performed, except that the number of twists of the refined silk was changed as shown in Table 2.

The results thereof are shown in Table 2.

Comparative Example 1

The same operations as those of Example 1 were performed, except that the raw silk was changed to cotton (a raw yarn extracted from QUEEN PEARL LACE #20 (a thread in which four raw yarns are intertwisted) manufactured by Yuzawaya Shoji Co., Ltd.).

The results thereof are shown in Table 2.

It is noted here that this cotton was a short fiber composed of cellulose. In addition, the cotton was a twisted yarn (see Table 2).

Comparative Example 2

The same operations as those of Example 1 were performed, except that the raw silk (27-denier raw yarn) was changed to a slit ribbon having an elongated flat-plate shape of 0.6 mm in width that was prepared by micro-slitting a polylactic acid film produced by the below-described method.

The results thereof are shown in Table 2.

<Production of Polylactic Acid Film>

As a helical chiral polymer (A), a polylactic acid manufactured by NatureWorks LLC (product name: INGEO™ BIOPOLYMER, brand: 4032D, weight-average molecular weight (Mw): 200,000, melting point (Tm): 166° C., glass transition temperature (Tg): from 57° C. to 60° C.) was used. This polylactic acid (100 parts by mass) and the below-described stabilizer X (1.0 part by mass) were dry-blended to prepare a raw material.

The thus obtained raw material was placed in a hopper of an extrusion molding machine, extruded from a T-die while being heated to a temperature of from 220° C. to 230° C., and then brought into contact with a 50° C. casting roll for 0.3 minutes, whereby a 0.15 mm-thick pre-crystallized sheet was formed (pre-crystallization step). The crystallization degree of this pre-crystallized sheet was measured to be 6%.

Stretching of the thus obtained pre-crystallized sheet was initiated at a stretching rate of 3 m/min in a roll-to-roll manner while heating the pre-crystallized sheet to 70° C., and the pre-crystallized sheet was uniaxially stretched in the MD direction to a stretching ratio of 3.5 times (stretching step). The thus obtained uniaxially stretched film had a thickness of 0.05 mm.

This uniaxially stretched film was brought into contact with a roll heated to 145° C. for 15 seconds in a roll-to-roll manner and thereby annealed, after which the thus annealed film was rapidly cooled to obtain a 0.05 mm-thick piezoelectric film (polylactic acid film) (annealing step).

TABLE 2

| | Piezoelectric body | | | | | | | | Evaluation (electrometer) | |
|---|---|---|---|---|---|---|---|---|---|---|
| | Core material Material | Material | Fiber type | Fiber form | Degree of orientation F | Winding direction | Helix angle (°) | Outer conductor | Piezoelectric sensitivity (pC/N · mm) | Sensitivity after environmental test (pC/N · mm) |
| Example 1 | tinsel wire | optically active polypeptide | silk (raw silk) | long fiber non-twisted yarn | 0.92 | Left | 45 | present | 0.3 | — |
| Example 2 | tinsel wire | optically active polypeptide | silk (raw silk) | long fiber non-twisted yarn | 0.92 | Right | 45 | present | −0.4 | — |
| Example 3 | tinsel wire | optically active polypeptide | silk (raw silk) | long fiber non-twisted yarn | 0.92 | Right | 25 | present | −0.1 | — |
| Example 4 | tinsel wire | optically active polypeptide | silk (raw silk) | long fiber non-twisted yarn | 0.92 | Right | 30 | present | −0.4 | — |
| Example 5 | tinsel wire | optically active polypeptide | silk (raw silk) | long fiber non-twisted yarn | 0.92 | Right | 60 | present | −0.4 | — |
| Example 6 | tinsel wire | optically active polypeptide | silk (raw silk) | long fiber non-twisted yarn | 0.92 | Right | 65 | present | −0.1 | — |
| Example 7 | tinsel wire | optically active polypeptide | silk (refined silk) | long fiber twisted yarn (150 T/m) | 0.90 | Right | 45 | present | −2.3 | −2.3 |
| Example 8 | tinsel wire | optically active polypeptide | silk (refined silk) | long fiber twisted yarn (200 T/m) | 0.90 | Right | 45 | present | −0.5 | — |
| Example 9 | tinsel wire | optically active polypeptide | silk (refined silk) | long fiber twisted yarn (300 T/m) | 0.90 | Right | 45 | present | −0.5 | — |
| Example 10 | tinsel wire | optically active polypeptide | silk (refined silk) | long fiber twisted yarn (400 T/m) | 0.90 | Right | 45 | present | −0.6 | — |

TABLE 2-continued

| | Piezoelectric body | | | | | | | | Evaluation (electrometer) | |
| --- | --- | --- | --- | --- | --- | --- | --- | --- | --- | --- |
| | Core material Material | Material | Fiber type | Fiber form | Degree of orientation F | Winding direction | Helix angle (°) | Outer conductor | Piezoelectric sensitivity (pC/N · mm) | Sensitivity after environmental test (pC/N · mm) |
| Comparative Example 1 | tinsel wire | cellulose | cotton | short fiber twisted yarn | 0.61 | Left | 45 | present | 0 | — |
| Comparative Example 2 | tinsel wire | optically active polyester | polylactic acid | slit ribbon | 0.97 | Left | 45 | present | 14 | 0 |

As shown in Table 2, piezoelectric sensitivity was observed in the piezoelectric substrates of Examples 1 to 10 in which a silk (raw silk or refined silk) including a fiber composed of an optically active polypeptide was used as a piezoelectric body and the length direction of the piezoelectric body and the main orientation direction of the optically active polypeptide included in the piezoelectric body were substantially parallel to each other.

On the other hand, piezoelectric sensitivity was not observed in Comparative Example 1 where the silk was changed to cotton.

Moreover, the silk that is a polypeptide has excellent hydrolysis resistance. Therefore, the piezoelectric substrates of Examples 1 to 10 were confirmed to have superior durability as compared to, for example, the piezoelectric substrate of Comparative Example 2 in which a polylactic acid-containing piezoelectric body was used (i.e., a piezoelectric substrate containing an optically active polyester).

Example 101

<Preparation of Piezoelectric Substrate (without Outer Conductor)>

As a piezoelectric body, the same silk (raw silk) as the one used in Example 1 was prepared.

As a core material, a meta-aramid fiber ("CONEX" manufactured by Teijin Ltd. (count: 40, fiber diameter: 0.12 mm, double-twisted, length: 150 mm)) was prepared.

Crimp terminals were caulked to the respective ends of the core material to arrange mechanical connectors on the respective ends of the core material. In this process, the distance between the two crimp terminals was set at 100 mm.

Next, the above-prepared raw silk (piezoelectric body) was helically wound around the core material with no gap such that the core material was not exposed.

In this process, the raw silk was wound at a helix angle (an angle with respect to the longitudinal direction of the core material) of 45° in a left-handed manner from the front side toward the back side along the axial direction of the core material).

Subsequently, as an adhesive, ARON ALPHA manufactured by Toagosei Co., Ltd. (cyanoacrylate-based adhesive) was dropped onto the resultant to impregnate the resultant with the adhesive, whereby the core material and the raw silk were bonded together and mechanically integrated.

A piezoelectric substrate was obtained in the above-described manner.

<Measurement of Piezoelectric Sensitivity of Piezoelectric Substrate (Surface Potential Meter)>

Using a surface potential meter, the piezoelectric sensitivity (V/N) of the thus obtained piezoelectric substrate was measured by the following method.

The result thereof is shown in Table 3.

—Method of Measuring Piezoelectric Sensitivity (V/N) of Piezoelectric Substrate (Surface Potential Meter)—

The piezoelectric substrate was chucked in a tensile tester (TENSILON RTG1250 manufactured by A&D Co., Ltd.) at a chuck distance of 100 mm. Specifically, the crimp terminal (mechanical connector) on one end of the piezoelectric substrate was chucked with one of the chuck members, and the crimp terminal (mechanical connector) on the other end of the piezoelectric substrate was chucked with the other chuck member.

Subsequently, using the tensile tester, a tension in a triangular wave form was periodically and repeatedly applied to the piezoelectric substrate in a stress range of from 1.0 N to 2.0 N, and the surface potential of the piezoelectric body in this process was measured using a surface potential meter (MODEL 541A-2 manufactured by TREK, Inc.).

It is noted here that the measurement was performed with the sensor head of the surface potential meter being arranged in the center between the chucks of the tensile tester and being close to the piezoelectric substrate to be measured at a distance of 1 mm in such a manner that the normal line of the circular end surface of the cylindrical sensor head was perpendicular to the piezoelectric substrate. Further, the chucked portions of the piezoelectric substrate and the tensile tester were electrostatically shielded by enclosing them with an aluminum metal plate, and the aluminum metal plate and the ground electrode of the surface potential meter were electrically connected.

The surface potential generated per unit tensile force was calculated from the slope of a correlation straight line of a scatter diagram prepared by plotting the measured surface potential difference $\Delta V$ [V] on the Y-axis and the tensile force of the sample F [N] on the X-axis, and the thus calculated value was defined as the piezoelectric sensitivity [V/N].

Example 102

The above-prepared raw silk (piezoelectric body) was helically wound around an imaginary helical axis (i.e., a central axis of a helical structure formed by the raw silk) with no gap. In this process, the raw silk was wound at a helix angle (an angle with respect to the imaginary helical axis) of 45° in a left-handed manner from the front side toward the back side along the imaginary helical axis).

Thereafter, as an adhesive, ARON ALPHA manufactured by Toagosei Co., Ltd. (cyanoacrylate-based adhesive) was dropped onto the raw silk to impregnate the raw silk with the adhesive, whereby the raw silk was mechanically integrated.

A piezoelectric substrate of 120 mm in length and 0.3 mm in thickness was obtained in the above-described manner.

The piezoelectric sensitivity (V/N) of the thus obtained piezoelectric substrate was measured in the same manner as in Example 101, except that one end of this piezoelectric substrate was chucked with one of the chuck members and the other end of this piezoelectric substrate was chucked with the other chuck member.

The result thereof is shown in Table 3.

Comparative Example 101

The same operations as those of Example 101 were performed, except that the raw silk was changed to cotton (a raw yarn extracted from QUEEN PEARL LACE #20 (a thread in which four raw yarns are intertwisted) manufactured by Yuzawaya Shoji Co., Ltd.).

The result thereof is shown in Table 3.

Subsequently, as an outer conductor, a copper foil ribbon that had been slit-cut at a width of 0.6 mm was wound and wrapped on the thus obtained braid with no gap such that the braid was not exposed.

Thereafter, in order to mechanically integrate the core material, the refined silk and the copper foil ribbon, as an adhesive, ARON ALPHA manufactured by Toagosei Co., Ltd. (cyanoacrylate-based adhesive) was dropped onto the resultant and the resultant was impregnated with the adhesive, whereby the core material, the refined silk and the copper foil ribbon were bonded together.

A piezoelectric substrate was obtained in the above-described manner.

TABLE 3

| | Core material | Piezoelectric body | | | | | | Evaluation (surface potential meter) |
| | Material | Material | Fiber type | Fiber form | Degree of orientaion F | Winding direction | Helix angle (°) | Outer conductor | Piezoelectric sensitivity (V/N) |
|---|---|---|---|---|---|---|---|---|---|
| Example 101 | meta-aramid fiber | optically active polypeptide | silk (raw silk) | long fiber long-twisted yarn | 0.92 | Left | 45 | none | 0.9 |
| Example 102 | none | optically active polypeptide | silk (raw silk) | long fiber long-twisted yarn | 0.92 | Left | 45 | none | 0.6 |
| Comparative Example 101 | meta-aramid fiber | cellulose | cotton | short fiber twisted yarn | 0.61 | Left | 45 | none | not observed |

As shown in Table 3, piezoelectric sensitivity was observed in the piezoelectric substrates of Examples 101 and 102 in which a silk (raw silk) was used as a piezoelectric body.

On the other hand, piezoelectric sensitivity was not observed in Comparative Example 101 where the silk (raw silk) was changed to cotton (i.e., cellulose-containing fiber).

Moreover, the silk that is a polypeptide has excellent hydrolysis resistance. Therefore, the piezoelectric substrates of Examples 101 and 102 are expected to have superior durability as compared to, for example, a piezoelectric substrate in which a polylactic acid-containing piezoelectric body is used.

Example 201

<Preparation of Piezoelectric Substrate (with Outer Conductor, Braided Structure)>

As a piezoelectric body, the same refined silk as the one used in Example 7 was prepared.

As a core material, a tinsel wire "U24-01-00" manufactured by Meisei Industry Co., Ltd. (wire diameter: 0.26 mm) was prepared.

Crimp terminals were caulked to the respective ends of the core material to arrange mechanical connectors on the respective ends of the core material. In this process, the distance between the two crimp terminals was set at 100 mm.

Next, around the core material, four non-piezoelectric polyester fibers (TETORON, 78 denier) and four refined silk fibers were knitted while winding them in a left-handed direction and a right-handed direction, respectively, whereby an 8-strand braid was prepared.

In this process, the helix angle of the refined silk (the angle with respect to the longitudinal direction of the core material) was controlled at 51°.

Example 202

A piezoelectric substrate was obtained in the same manner as in Example 201, except that the helix angle of the refined silk was controlled at 45°.

<Measurement of Piezoelectric Sensitivity of Piezoelectric Substrate (Electrometer)>

Using an electrometer, the piezoelectric sensitivity (pC/N·mm) of the thus obtained piezoelectric substrate was measured by the following method.

The result thereof is shown in Table 4.

—Method of Measuring Piezoelectric Sensitivity (pC/N·mm) of Piezoelectric Substrate (Electrometer)—

The piezoelectric substrate was chucked in a tensile tester (TENSILON RTG1250 manufactured by A&D Co., Ltd.) at a chuck distance of 150 mm. Specifically, the crimp terminal (electrical and mechanical connector) on one end of the piezoelectric substrate was chucked with one of the chuck members, and the crimp terminal (electrical and mechanical connector) on the other end of the piezoelectric substrate was chucked with the other chuck member. Further, the charge measuring electrodes of an electrometer (617 manufactured by Keithley Instruments, Inc.) were connected to the crimp terminals of the piezoelectric substrate, and the ground electrode of the electrometer (617 manufactured by Keithley Instruments, Inc.) was connected to the outer conductor (copper foil ribbon) of the piezoelectric substrate.

Subsequently, using the tensile tester, a tension in a triangular wave form was periodically and repeatedly applied to the piezoelectric substrate in a stress range of from 1 N to 2 N at a frequency of 0.2 Hz, and the amount of charge generated on the core material side of the piezoelectric body (raw silk) in this process was measured using the electrometer (617 manufactured by Keithley Instruments, Inc.).

The amount of generated charge per unit tensile force was calculated from the slope of a correlation straight line of a scatter diagram prepared by plotting the measured amount of generated charge Q [C] on the Y-axis and the tensile force of the piezoelectric substrate F [N] on the X-axis, and the thus calculated value was divided by the distance between the crimp terminals to determine the piezoelectric sensitivity (pC/N·mm).

<Evaluation of Temperature Characteristic (Measurement of Sensitivity (pC/N·mm) at 80° C.)>

For the piezoelectric substrates of Examples 202 and Comparative Example 2, a temperature characteristic was evaluated by the following method.

Specifically, after measuring the initial piezoelectric sensitivity (pC/N mm) in the above-described "Measurement of Piezoelectric Sensitivity of Piezoelectric Substrate (Electrometer)", test pieces of the piezoelectric substrates were hung and retained in an incubator maintained at 80° C. (humidity: 25% RH) for a prescribed period (30 minutes). Then, for each of these test pieces, the piezoelectric sensitivity (pC/N·mm) was determined in the same manner as the above-described "Method of Measuring Piezoelectric Sensitivity (pC/N·mm) of Piezoelectric Substrate (Electrometer)", and the thus obtained value was defined as "sensitivity at 80° C. (pC/N·mm)". The results thereof are shown in Table 5.

The disclosure of Japanese Patent Application No. 2016-225366 filed on Nov. 18, 2016, is hereby incorporated by reference in their entirety.

All the documents, patent applications and technical standards that are described in the present specification are hereby incorporated by reference to the same extent as if each individual document, patent application or technical standard is concretely and individually described to be incorporated by reference.

The invention claimed is:

1. A piezoelectric material, comprising
an elongated piezoelectric body that is helically wound, wherein
the piezoelectric body includes an optically active polypeptide,
the optically active polypeptide comprises an animal protein having an optical activity,
a length direction of the piezoelectric body and a main orientation direction of the optically active polypeptide included in the piezoelectric body are substantially parallel to each other, and
the piezoelectric body has a degree of orientation F of from 0.50 to less than 1.00, as determined from X-ray diffraction measurement by the following Formula (a):

$$\text{Degree of orientation } F=(180°-\alpha)/180° \tag{a}$$

TABLE 4

| | Core material | Piezoelectric body | | | | | | Evaluation (electrometer) Piezoelectric sensitivity (pC/N · mm) |
|---|---|---|---|---|---|---|---|---|
| | Material | Material | Fiber type | Fiber form | Degree of orientation F | Winding direction | Helix angle (°) | Outer conductor | |
| Example 201 | tinsel wire | optically active polypeptide | silk (refined silk) | long fiber twisted yarn (150 T/m) | 0.90 | Right | 51 | present | −0.2 |
| Example 202 | tinsel wire | optically active polypeptide | silk (refined silk) | long fiber twisted yarn (150 T/m) | 0.90 | Right | 45 | present | −0.4 |

TABLE 5

| | Evaluation (electrometer) | |
|---|---|---|
| | Piezoelectric sensitivity (pC/N · mm) | Sensitivity at 80° C. (pC/N · mm) |
| Example 202 | −0.4 | −0.4 |
| Comparative Example 2 | 14 | 2.3 |

As shown in Tables 4 and 5, piezoelectric sensitivity was observed in the piezoelectric substrates of Examples 201 and 202 in which a silk (refined silk) including a fiber composed of an optically active polypeptide was used as a piezoelectric body and the length direction of the piezoelectric body and the main orientation direction of the optically active polypeptide included in the piezoelectric body were substantially parallel to each other.

Moreover, the silk that is a polypeptide has excellent hydrolysis resistance. Therefore, the piezoelectric substrate of Example 202 was confirmed to have superior temperature characteristic (i.e., a lower temperature dependence of the piezoelectric sensitivity) as compared to, for example, the piezoelectric substrate of Comparative Example 2 in which a polylactic acid-containing piezoelectric body was used (i.e., a piezoelectric substrate containing an optically active polyester).

wherein, in Formula (a), α represents a half width (°) of a peak derived from orientation.

2. The piezoelectric material according to claim 1, wherein the elongated piezoelectric body is helically wound in a single direction.

3. The piezoelectric material according to claim 1, further comprising an elongated core material, wherein the elongated piezoelectric body is helically a wound around the elongated core material.

4. The piezoelectric material according to claim 3, wherein the elongated core material is a conductor.

5. The piezoelectric material according to claim 3, comprising an outer conductor on an outer peripheral side of the elongated piezoelectric body, wherein the elongated core material and the outer conductor are electrically insulated from each other.

6. The piezoelectric material according to claim 1, comprising no core material.

7. The piezoelectric material according to claim 1, wherein the optically active polypeptide has a β sheet structure.

8. The piezoelectric material according to claim 1, wherein the elongated piezoelectric body comprises a fiber that is composed of the optically active polypeptide.

9. The piezoelectric material according to claim 1, wherein the optically active polypeptide comprises at least one of fibroin or a spider silk protein.

10. The piezoelectric material according to claim 8, wherein the fiber that is composed of the optically active polypeptide comprises at least one of a silk or a spider silk.

11. The piezoelectric material according to claim 10, wherein the silk is refined silk.

12. The piezoelectric material according to claim 1, wherein
the elongated piezoelectric body is composed of a fiber that is composed of the optically active polypeptide, and
the fiber is a yarn having a number of twists of 500 T/m or less.

13. The piezoelectric material according to claim 1, wherein the elongated piezoelectric body is wound at a helix angle of from 20° to 70°.

14. The piezoelectric material according to claim 1, comprising an insulator on the outermost periphery.

15. A sensor comprising the piezoelectric material according to claim 1.

16. An actuator comprising the piezoelectric material according to claim 1.

17. A biological information acquisition device comprising the piezoelectric material according to claim 1.

18. A piezoelectric fiber structure comprising:
a first piezoelectric body comprising a first piezoelectric material, which is the piezoelectric, material according to claim 1; and
a second piezoelectric body comprising a second piezoelectric material, which is the piezoelectric material according to claim 1, in which an optically active polypeptide included in the second piezoelectric body has same chirality as an optically active polypeptide included in the first piezoelectric body of the first piezoelectric material, and a winding direction of the second piezoelectric body is opposite to that of the first piezoelectric body of the first piezoelectric material.

19. A piezoelectric fiber structure comprising:

a first piezoelectric body comprising a first piezoelectric material, which is the piezoelectric material according to claim 1; and a second piezoelectric body comprising a second piezoelectric material, which is the piezoelectric material according to claim 1, in which an optically active polypeptide included in the second piezoelectric body has a chirality that is different from that of an optically active polypeptide included in the first piezoelectric body of the first piezoelectric material, and a winding direction of the second piezoelectric body is the same as that of the first piezoelectric body of the first piezoelectric material.

* * * * *